United States Patent [19]
Kramer et al.

[11] Patent Number: 5,503,979
[45] Date of Patent: Apr. 2, 1996

[54] METHOD OF USING REPLICATABLE HYBRIDZABLE RECOMBINANT RNA PROBES

[75] Inventors: Fred R. Kramer, New York, N.Y.; Paul M. Lizardi, Ouernavaca, Mexico

[73] Assignee: The Trustees of Columbia University in the City of New York, New York, N.Y.

[21] Appl. No.: 296,866

[22] Filed: Aug. 26, 1994

Related U.S. Application Data

[63] Continuation of Ser. No. 118,476, Sep. 8, 1993, abandoned, which is a continuation of Ser. No. 988,356, Dec. 9, 1992, abandoned, which is a continuation of Ser. No. 527,585, May 23, 1990, abandoned, which is a continuation-in-part of Ser. No. 256,746, Oct. 12, 1988, abandoned, which is a division of Ser. No. 614,350, May 25, 1984, Pat. No. 4,786,600, and a continuation-in-part of Ser. No. 183,838, Apr. 20, 1988, abandoned, and Ser. No. 852,692, Apr. 16, 1986, Pat. No. 4,957,858.

[51] Int. Cl.⁶ .............................. C12Q 1/68; C12P 19/34
[52] U.S. Cl. .......................... 435/6; 435/91.1; 435/91.2; 435/91.21; 435/91.3; 435/91.32; 435/91.5; 435/172.3; 435/948; 436/501; 536/23.1; 536/24.1; 536/24.3; 536/24.31; 536/24.32; 536/24.33; 935/17; 935/31; 935/78; 935/88
[58] Field of Search ................................. 435/5, 6, 91.1, 435/91.2, 91.21, 91.3, 91.32, 91.5, 91.51, 172.3, 948; 436/501, 815; 536/22.1, 23.1, 24.1, 24.3–24.33, 25.3; 935/17, 31, 77, 78, 88

[56] References Cited

U.S. PATENT DOCUMENTS

| | | | |
|---|---|---|---|
| 3,444,044 | 5/1969 | Spiegelman et al. | 195/28 |
| 4,786,600 | 11/1988 | Kramer et al. | 435/235 |
| 4,957,858 | 9/1990 | Chu et al. | 435/6 |

FOREIGN PATENT DOCUMENTS

| | | | |
|---|---|---|---|
| 346594 | 12/1989 | European Pat. Off. | |
| WO8706270 | 10/1987 | WIPO | |
| WO9002819 | 3/1990 | WIPO | |

OTHER PUBLICATIONS

Miele et al. (1983) J. Mol. Biol, vol. 171, pp. 281–295.
Miele (1982) Ph.D. Thesis University Microfilms, Ann Arbor, Mich. (Exhibit A).
Miele, et al. (1982) 11th Annual Cetus–UCLA Symp. on Gene Regulation Supp. p. 314 (Exhibit B).
Shen et al. (1982) Scientia Sinica (Ser. B.), pp. 485–495 (Exhibit C).
Nishihara, et al. (1983) J. Biochem. 93:669–674 (Exhibit D).
Bausch, et al. (1983) J. Biol. Chem. 258:1978–1984 (Exhibit E).
Obinata, et al. (1975) Biochem. and Biophys. Res. Comm. 64(2):640–647 (Ex. H).
Chu et al. (1986) Nucleic Acids Research 14(14):5591–5603 (Exhibit I).
Kramer et al. (1978) PNAS 75(11):5334–5338 (Exhibit M).
Urdea et al. (1987), Gene 61:253–264 (Exhibit N).
Langdale, et al. (1985), Gene 36:201–210 (Exhibit O).
Mills et al. (1980), Biochemistry 19(1):228–236 (Exhibit P).

*Primary Examiner*—Stephanie W. Zitomer
*Assistant Examiner*—Ardin H. Marschel
*Attorney, Agent, or Firm*—John P. White

[57] ABSTRACT

The present invention provides a replicatable and hybridizable recombinant single-stranded RNA probe molecule comprising: a recognition sequence for the binding of an RNA-directed RNA polymerase; a sequence required for the initiation of product strand synthesis by the polymerase; and a heterologus RNA sequence inserted at a specific site in the internal region of the recombinant molecule and complementary to an oligo or polynucleotide of interest. This invention also provides methods for determining the presence of concentration of an oligo- or polynucleotide of interest in a sample and for simultaneously determining the presence or concentration of several different oligo- or polynucleotides of interest in a sample.

26 Claims, 13 Drawing Sheets

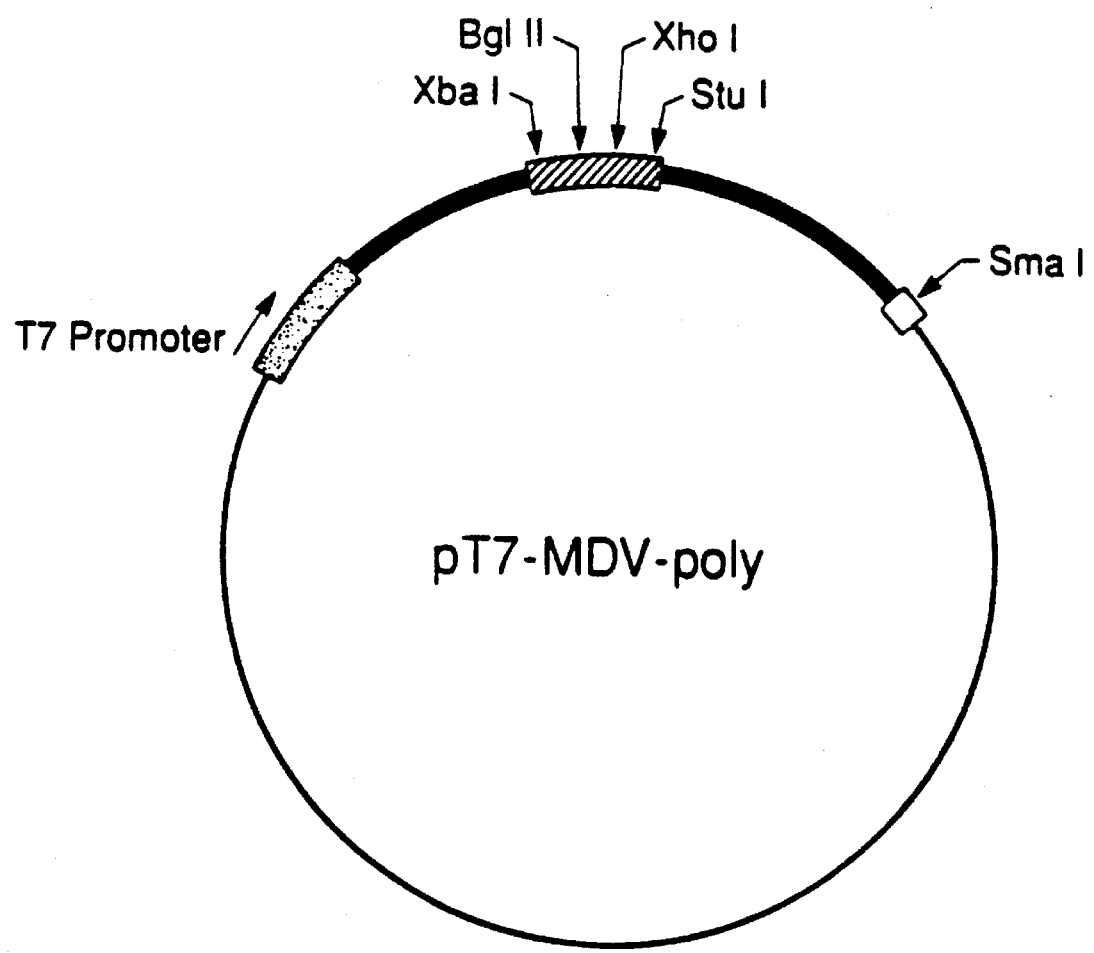

5,503,979

METHOD OF USING REPLICATABLE HYBRIDZABLE RECOMBINANT RNA PROBES

This invention described herein was made in the course of work under Grant No. DMB-86-16429 from the National Science Foundation and Grant No. GM-33345 from the National Institutes of Health, U.S. Department of Health and Human Services. The U.S. Government has certain rights in this invention.

This application is a continuation of U.S. Ser. No. 118,476; filed Sep. 8, 1993, and now abandoned; which is a continuation of U.S. Ser. No. 988,356; filed Dec. 9, 1992, and now abandoned; which is a continuation of U.S. Ser. No. 527,585; filed May 23, 1990, and now abandoned; which is a continuation-in-part of U.S. Ser. No. 183,838; filed Apr. 20, 1988, and now abandoned; and U.S. Ser. No. 852,692; filed Apr. 16, 1986, now U.S. Pat. No. 4,957,858; issued Sep. 18, 1990; and U.S. Ser. No. 256,746; filed Oct. 12, 1988, and now abandoned; which is a divisional of U.S. Ser. No. 614,350; filed May 25, 1984; now U.S. Pat. No. 4,786,600; issued Nov. 22, 1988.

BACKGROUND OF THE INVENTION

Throughout this application, various publications are referenced and citations provided for them. The disclosure of these publications in their entireties are hereby incorporated by reference into this application to more fully describe the state of the art to which this invention pertains.

It is now a well established fact that all living organisms including infectious agents, e.g., viruses, contain DNA, or sometimes RNA, molecules which carry genetic information in the form of a nucleotide sequence code. While certain segments of this code are shared by many organisms, there are other segments which contain nucleotide sequences that are unique for a particular organism. These sequences are said to be species-specific and provide a convenient tag or footprint that can be utilized for identification of that organism. The technique of nucleic acid hybridization (Gillespie and Spiegelman, 1965) has great potential for the rapid detection and typing of infectious agents. However, current hybridization assays have not yet attained the sensitivity and speed required for practical diagnostic use. It has recently been proposed that the sensitivity and speed of bioassays could be improved by linking a replicatable RNA to a hybridization probe (Chu, et al. 1986). After hybridization, the replicatable RNA would be amplified by incubation with the RNA-directed RNA polymerase, Qβ replicase (Haruna and Spiegleman, 1965a). The enormous number of RNA copies that would be synthesized would serve as a signal that hybridization had occurred. The synthesis of novel nucleic acid hybridization probes that combine in a single RNA molecule the dual functions of probe and amplifiable reporter is described in this invention.

A distinguishing feature of RNA synthesis by Qβ replicase is that a small number of template strands can initiate the synthesis of a large number of product strands (Haruna and Spiegleman, 1965b). Million-fold increases in the amount of RNA routinely occur in vitro (Kramer, et al. 1974) as a result of an autocatalytic reaction mechanism (Weissmann, et al. 1986; Spiegelman, et al. 1968): single-stranded RNAs serve as templates for the synthesis of complementary single-stranded products; after the completion of product strand elongation, both the product and the template are released from the replication complex (Dobkin, et al. 1979); and both strands are free to serve as templates in the next round of synthesis. Consequently, as long as there is an excess of replicase, the number of RNA strands increases exponentially. After the number of RNA strands equals the number of active replicase molecules, RNA synthesis continues linearly.

Qβ replicase was first isolated from bacteriophage Qβ-infected *Escherichia coli* by Haruna and Spiegelman (1965a). It is composed of four polypeptides, only one of which is specified by the viral RNA. The other three polypeptides are *E. coli* proteins, and have been identified as the protein synthesis elongation factors Tu and Ts and the ribosomal protein S1. When provided with the single-stranded RNA from Qβ, the replicase mediates the exponential synthesis of infectious viral RNA (Spiegelman et al., 1965). The enzyme is highly template selective. No other viral RNA, nor any *E. coli* RNA, will serve as a template (Haruna and Spiegelman, 1965c). When RNA from a temperature-sensitive mutant of Qβ was used as a template with wild-type replicase, mutant RNA was synthesized, demonstrating that the template is the instructive agent (Pace and Spiegelman, 1966). The replicative process (Spiegelman et al., 1969; Weissmann et al., 1968) proceeds in the following manner: The replicase uses the viral (+) strand as a template to direct the synthesis of a complementary (−) strand. Both of these strands serve as templates for the synthesis of additional (+) and (−) strands; and exponential increase is observed in the number of RNA strands present. Eventually, there are enough strands to saturate the available enzyme molecules, after which the number of strands increases linearly with time. Because of the complementary nature of this process, it is often referred to as "self-replication". There are a number of advantages to using the amplification of RNA by Qβ replicase as the basis of a signal-generating system: Qβ replicase is highly specific for its own template RNAs (Haruna and Spiegelman, 1965c); as little as one molecule of template RNA can, in principle, initiate replication (Levisohn and Spiegelman, 1968); and the amount of RNA synthesized (typically, 200 ng in 50 λl in 15 minutes) is so large that it can be measured with the aid of simple colorimetic techniques.

There are a number of naturally occurring Qβ replicase templates that are much smaller than Qβ RNA. These RNAs have been isolated from in vitro Qβ replicase reactions that were incubated in the absence of exogenous template RNA. They include: MDV-1 RNA (Kacian et al., 1972), microvariant RNA (Mills et al., 1975), the nanovariant RNAs (Schaffner et al., 1977), RQ120 RNA (Munishkin et. al., 1989), and cordycepin-tolerant RNA (Priano et al., 1989). Although the origin and biological role of these RNAs is not known, they have been extensively characterized and are all excellent templates for Qβ replicase.

Isolated MDV-1 RNA serves as an excellent exogenous template. It is bound by Qβ replicase and replicated in a manner similar to Qβ RNA (Kacian et al., 1972). MDV-1 RNA is much smaller (221 nucleotides) than Qβ RNA (4,220 nucleotides), which led to the determination of its complete nucleotide sequence (Mills et al., 1973; Kramer and Mills, 1978).

Two striking aspects of the MDV-1 sequence are its unusually high proportion of guanosine and cytidine residues and the occurrence of many intrastrand complements capable of forming hairpin structures. MDV-1 has been directly visualized (Klotz et al., 1980), utilizing hollow-cone, dark-field electron microscopy. Observations made with native, partially denatured, and fully denatured molecules indicate that native single-stranded MDV-1 RNA is a highly condensed molecule, possessing substantial tertiary structure. Specific secondary structures were identified by reacting MDV-1RNA with chemical agents that modify single-stranded regions (Mills et al., 1980). The location of the altered nucleotides was determined by sequencing the modified RNA. The tertiary structure of MDV-1 RNA was probed by subjecting it to mild cleavage with ribonuclease $T_1$ (Kramer et al., 1989), which only cleaves single-stranded regions. Because of the extensive secondary and tertiary structure present in MDV-1 RNA, combined with the macromolecular dimensions of ribonuclease $T_1$, the initial sites of attack were limited to those on the exterior of the molecule. The few guanosines in each strand that were hypersusceptible to ribonuclease $T_1$ were located in hairpin loops.

A more detailed understanding of the mechanism of MDV-1 RNA synthesis was facilitated by the development of an electrophoretic technique for separating the complementary strands (Mills et al., 1978). An excess of pure MDV-1 (−) RNA was used as template in the presence of a small amount of Qβ replicase, in a series of experiments designed to elucidate the synthetic cycle. Mutant MDV-1 (−) RNA (Kramer et al., 1974) was added to these reactions after the initiation of chain elongation to see whether replicase molecules retain the same template through many rounds of synthesis. It was shown that a single replicase molecule bound to a single template strand is sufficient to carry out a complete synthetic cycle. It was shown that after the completion of each round of chain elongation, the product strand is released from the replication complex, and the template and the replicase then dissociate (Dobkin et al., 1979).

Specific regions of MDV-1 RNA are required by Qβ replicase to carry out different replication functions. A highly structured region in the middle of each complementary strand must be present for the replicase to bind to MDV-1 RNA. Utilizing a series of different-length fragments of MDV-1 RNA that were missing sequences at either their 5' end or their 3' end, the binding region was localized by assaying their ability to be bound by the replicase (Nishihara et al., 1983). Only fragments containing the central recognition region formed a complex. This region contains hairpins that were found to be hypersusceptible to ribonuclease $T_1$ cleavage (Kramer et al., 1989), and is therefore situated on the exterior of the molecule.

A particular sequence at 3' end of the template strand is required for the initiation of product strand synthesis. MDV-1RNA fragments lacking nucleotides at their 5' end were able to serve as templates for the synthesis of complementary strands, but fragments lacking nucleotides at their 3' end were unable to serve as templates, even though they were able to form complexes with the replicase (Nishihara et al., 1983). The sequence required for initiation to occur includes at least some of the 3' terminal cytidines, since the conversion of these cytidines to uridines by sodium bisulfite treatment was accompanied by a concomitant loss in the ability of the RNA to initiate synthesis (Mills et al., 1980). In a control experiment, MDV-1 (+) RNA was completely modified by bisulfite treatment, except for the 3'-terminal cytidines, which were protected by a complementary oligonucleotide mask. The resulting RNA was able to initiate synthesis. The 5' end of the template need not be present for the synthesis of multiple copies of complementary RNA (Bausch et al., 1983). However, it must be present if exponential synthesis is to occur, because the 5' terminal sequence serves as the template for the required 3' initiation sequence in the product strand.

Art exhaustive comparison of the nucleotide sequence of MDV-1 RNA and Qβ RNA (Nishihara et al., 1983) found only two significant homologies. These regions encompass the internal replicase binding site required for template recognition and the cytidine-rich 3'-terminal sequence required for product strand initiation.

Template secondary structures strongly influence the rate of chain elongation. Electrophoretic examination of the distribution of different-length elongation intermediates during the synthesis of MDV-1 RNA indicated that the rate of synthesis is highly variable (Mills et al., 1978). The data suggest that at a relatively small number of specific sites the progress of the replicase is temporarily interrupted, and then resumes spontaneously with a finite probability. The time spent at each of these pause sites is so long that the mean time it takes to replicate an RNA is well approximated by the sum of the mean times spent at each site. Nucleotide sequence analysis of the most prominent elongation intermediates indicated that each could form a strong 3'-terminal hairpin structure. This suggests that the marked variability in the rate of chain elongation is due to the formation of terminal hairpins in the product strand, or the reformation of hairpins in the template strand. Secondary structures that form during chain elongation are free to dissociate and form stronger secondary structures as nucleotides are added to the growing product strand (Kramer and Mills, 1981). Since the formation of secondary structures apparently slows down the rate of polymerization, their presence in the RNA, per se, is disadvantageous, and they should not have evolved. These structures must therefore confer a selective advantage that outweighs their negative effect on the rate of synthesis. Recent experiments that compared the replication of cordycepin-tolerant RNA to the replication of MDV-1 RNA and microvariant RNA have shown that the formation of these secondary structures during chain elongation is required to prevent the collapse of the product strand upon the template strand (Priano et al., 1987).

Many investigators have wished to exploit the autocatalytic nature of Qβ replicase reactions to synthesize large amounts of any RNA in vitro. However, Qβ replicase cannot copy most RNAs. It is highly selective for its own naturally occurring templates. Two specific interactions between the replicase and the template RNA account for this specificity. The replicase binds to the template at the internal recognition sequence, and the cytidine-rich sequence at the 3' end of the template is required for the initiation of product strand synthesis. Each of these sequences must be present in an RNA for exponential synthesis to occur. The exponential synthesis of heterologous RNAs was achieved by constructing recombinant RNAs by the insertion of heterologous sequences at an appropriate site within MDV-1 RNA (Miele et al., 1983). The insertion site chosen (between nucleotides 63 and 64 of MDV-1 (+) RNA) was located away from the regions that are required for template recognition and product strand initiation. The site was in hairpin loop, where it was least likely to disturb structure; and it was in a loop where viable mutations were known to occur, indicating that the sequence in that region was not essential for replication. Furthermore, this site was located on the exterior of the molecule in a hairpin loop that was hypersusceptible to cleavage by ribonuclease $T_1$. The first recombinant RNA constructed was prepared by cleaving MDV-1 (+) RNA at the selected site with ribonuclease $T_1$ and then inserting decaadenylic acid there by direct ligation with the aid of bacteriophage T4 RNA ligase. The resulting 231-nucleotide recombinant was an excellent template for Qβ replicase, demonstrating that the inserted sequence did not interfere with replication. The products consisted of full-length copies of the recombinant RNA, and both complementary strands were synthesized. An analysis of the kinetics of recombinant RNA synthesis demonstrated that the amount of recombinant RNA increased exponentially at a rate that was indistinguishable from that of MDV-1 RNA.

A plasmid that contains a strong bacteriophage T7 promoter (Lizardi et al., Mills et al., 1990) directed towards the MDV-1 cDNA sequence is a good template for MDV-1 RNA synthesis (Axelrod and Kramer, 1985). Bacteriophage RNA polymerases are highly specific for their own promoters (Chamberlin and Ring, 1973). Incubation with a bacteriophage RNA polymerase results in the exclusive transcription of the nucleotide sequence immediately downstream from its homologous promoter (McAllister et al., 1981; Melton et al., 1984). Moreover, the transcripts are virtually homogenous; and as many as 300 transcripts can be synthesized from each promoter in a 30 minute incubation.

The two developments discussed supra led to the present invention, namely, the discovery that heterologous RNA segments can be inserted within the sequence of a small, naturally occurring template for Qβ replicase, MDV-1 RNA (Kacian, et al. 1972), without affecting its replicability Miele, 1983 (Miele, et al. 1983); and the construction of a plasmid that serves as a template for the synthesis of MDV-1 (+) RNA when the plasmid is incubated in vitro with bacteriophage T7 RNA polymerase (Mills, et al. 1990).

This plasmid has been modified in the present invention by inserting a polylinker within the MDV-1 cDNA sequence, and then inserting synthetic hybridization probe sequences within the polylinker. The resulting plasmids served as templates for the synthesis of "recombinant RNAs," which consist of a probe sequence embedded within the sequence of MDV-1 (+) RNA. The site for inserting the polylinker and probe into MDV-1 RNA is on the exterior of the molecule to reduce any possible interference with replication and hybridization of the probe sequence to its target. The probe sequences employed in this invention and which will be further described in the Experimental Details section to follow, are known to hybridize specifically to the repetitive DNA of *Plasmodium falciparum* (Franzen, et al. 1984; Aslund, et al. 1985; Zolg, et al. 1987), one of the protozoans that cause malaria, and to a conserved region of the HIV-1 pol gene. These recombinant RNA molecules are bifunctional, in that they are able to hybridize specifically to complementary DNA targets and they are also able to serve as templates for exponential amplification by Qβ replicase.

Infectious agents may be quite rare in asymptomatic individuals who are infectious to others. For example, an asymptomatic individual may have as few as one in 100,000 peripheral blood mononuclear cells infected with the pathogenic retrovirus, human immunodeficiency virus type 1 (HIV-1), yet donated blood from that person will readily infect others (Harper, et al. 1986). It is thus imperative that very sensitive clinical assays be developed for detecting HIV-1, to screen donated blood and to identify asymptomatic carriers. Suitable assays would make use of a macromolecular probe having extremely high affinity for a particular component of the infections agent and very low affinity for all the other components of the sample. The highest specificities and most stable interactions known occur when a single-stranded oligonucleotide probe hybridizes to a complementary oligonucleotide target (Gillespie and Spiegelman, 1965). For example, oligonucleotide probes can seek out and bind to the integrated HIV-1 DNA, or the retroviral messenger RNA, present in a single infected cell.

However, the use of oligonucleotide probes is not sufficient to ensure detection. An infected cell contains only about 6000 molecules of retroviral messenger RNA (Pelligrino, et al. 1987), so the problem becomes how to detect the probes once they are bound to such a small number of targets. The classic detection strategy is to attach reporter groups to the probes, such as fluorescent organic molecules or radioactive phosphate groups. More recently, biotin groups have been incorporated into probes (Langer, et al. 1981). After the probes have bound to their targets, enzymes such as peroxidase or phosphatase are linked to the biotin, then incubated with a colorless substrate, leading to the accumulation of a large number of colored product molecules for each enzyme-probe adduct (Leary, et al. 1983). However, the practical limit of detection of these schemes is about $10^6$ target molecules. Clearly, they cannot be used to detect a single cell in a sample that contains only 6000 retroviral messenger RNAs.

A particularly attractive strategy for detecting rare targets is to link each probe to a replicatable reporter, which can be exponentially amplified after hybridization to reveal the presence of the probe (Chu, et al. 1986). The present invention concerns a novel version of this approach, in which a probe sequence is embedded within the sequence of a replicatable RNA (Lizardi, et al. 1988). The resulting recombinant RNAs hybridize to their target sequences as ordinary hybridization probes do and, as in a classical hybridization assay, nonhybridized probes are then washed away. The hybridized probes are then freed from their targets and released into solution. What makes these recombinant-RNA probes particularly useful is that they can then be exponentially amplified by incubation with the RNA-directed RNA polymerase, Qβ replicase (Haruna and Spiegelman, 1965). As many as $10^9$ copies of each replicatable probe can be synthesized in a single 30-minute incubation (Lizardi, et al. 1988). Furthermore, the extreme specificity of Qβ replicase for its own template RNA (Haruna and Spiegelman, 1965) assures that only the replicatable probes will be amplified. The large number of copies synthesized can easily be quantitated by incorporating radioactive nucleotides or by measuring the fluorescence of an intercalating dye such as ethidium bromide. Because as little as a single molecule of RNA can initiate exponential amplification (Levisohn and Spielelman, 1968), this approach offers the prospect of developing sensitive diagnostic assays.

The present invention provides an assay designed to detect very small amounts of HIV-1 mRNA. The assay format was designed to meet these criteria: (a) because of the desirability of developing a method that can screen a large number of samples, the selected format has to be fast and simple, thus precluding the fractionation of cells or the isolation of nucleic acids, and necessitating the use of solution hybridization; and (b) because nonhybridized probes are amplified by Qβ replicase along with hybridized probes, the format must include an extremely efficient means of removing the nonhybridized probes. Hybridization is extremely efficient in solutions of the chaotropic salt, guanidine thiocyanate (Thompson and Gillespie, 1987), and concentrated solutions of guanidine thiocyanate will lyse cells, denature all proteins (including nucleases), liberate nucleic acids from cellular matrices, and unwind DNA molecules, permitting hybridization to occur without interference from cellular debris (Pelligrino, et al. 1987). The "reversible target capture" procedure (Morrisey, et al. 1989) is an efficient means for removing nonhybridization probes. In this improved "sandwich hybridization" technique (Ranki, et al. 1983; Syvanen, et al. 1986), probe-target hybrids are bound to the surface of paramagnetic particles. After the particles are washed to remove nonhybridized probes, the hybrids are released from the particles, and then bound to a new set of particles for another washing. Repeating this procedure several times dramatically reduces the concentration of nonhybridized probes (Morrissey, et al. 1989).

It is imperative that sensitive tests be developed for the detection of human retroviruses.. Exogenously acquired retrovirus infections have been shown to be pathogenic. Human T-lymphotropic virus type I (HTLV-I) (Poiesz et al., 1980) and type II (HTLV-II) (Kalyanaraman et al., 1982) induce the transformation and proliferation of immature T lymphocytes, causing T-cell leukemia/lymphoma; and human immunodeficiency virus type 1 (HIV-1) (Popovic et al., 1984) and type 2 (HIV-2) (Clavel et al., 1986) induce a T-cell cytopathology that depletes T4 cells, causing acquired immune deficiency syndrome (AIDS). Human retroviruses are transmitted by contaminated blood and blood products and by sexual contact (Curran et al., 1985; Fauci, 1986). In addition, children may be infected perinatally or transplacentally; and intravenous drug abusers spread infection by sharing contaminated hypodermic needles. It is thus essential that effective procedures be developed for the detection of all known pathogenic retroviruses, in order to screen donated blood and to identify asymptomatic individuals who are carriers.

This invention also concerns the development of extremely sensitive assays for the detection of blood cells infected with pathogenic retroviruses. The assays utilize novel recombinant RNAs that serve as specific hybridization probes and also serve as templates for their own exponential amplification by Qβ replicase. Since more than one billion copies of each hybridized recombinant-RNA probe can be synthesized in a short incubation, extreme sensitivities can be achieved. These assays can be used to routinely screen donated blood and to identify asymptomatic individuals who are carriers, to prevent the spread of retroviral diseases.

Another method of detecting a small number of targets is the polymerase chain reaction (Saiki et al., 1985; Mullis and Faloona, 1987). In this scheme, oligonucleotide probes bind to targets and then serve as primers for DNA polymerase. Since as many as a million copies of each target region can be generated, great sensitivity can be achieved. Moreover, probes that are not bound to their targets cannot be elongated, so their presence does not generate a background signal. However, there are a number of significant disadvantages to using the polymerase chain reaction: DNA polymerase is inhibited by many components of the sample. For example, hemoglobin interferes with amplification; consequently, peripheral blood mononuclear cells must be separated from other cells prior to amplification. Alternatively, cellular DNA is isolated prior to analysis. Although greater sensitivity can be achieved by detecting retroviral messenger RNA, DNA polymerase cannot copy RNA, necessitating an additional reverse transcription step. Furthermore, each cycle of amplification involves incubation at two different temperatures, necessitating the use of a relatively expensive "temperature cycler"; and the 20 or more cycles needed for each assay consume time. The amount of DNA that can be synthesized with a given pair of primers is apparently limited by unidentified factors in the reaction to approximately one million copies of each target. Furthermore, when several primer pairs are used in a single assay (to detect different targets simultaneously), the amplification of each target is suppressed, resulting in markedly lower yields. Finally, the amplified DNA products frequently include a variety of unrelated background DNAs, necessitating an electrophoretic analysis or an additional hybridization to identify the desired DNA (Abbott et al., 1988). Although a variety of schemes exist to surmount these drawbacks, practical assays are likely to be rather cumbersome, time-consuming, and expensive.

In Kramer, et al., U.S. Pat. No. 4,786,600, issued Nov. 22, 1988, there are disclosed replicatable recombinant single-stranded RNA molecules comprising a recognition sequence for the binding of an RNA-directed RNA polymerase, a sequence for the initiation of product strand synthesis by the polymerase and a heterologous sequence of interest derived from a different RNA molecule inserted at a specific site in the internal region of the recombinant molecule. Kramer, et al. does not teach or suggest that if the inserted sequence is a hybridization probe sequence, that the resulting molecules can be replicated after hybridization to produce multiple copies for detection.

In Chu, et al., U.S. Pat. No. 4,957,858, issued Sep. 18, 1990, methods are disclosed for determining the presence of targets, i.e., analytes, by linking a replicatable RNA, which serves as a reporter group, to a probe, e.g., an oligonucleotide, an antibody or lectin. Chu, et al. also disclose that an RNA-directed RNA polymerase can then be used after hybridization has occurred to produce multiple copies of the replicatable RNA for detection. However, Chu, et al. do not describe a method in which different recombinant-RNA "probe" sequences can be used simultaneously in the same assay.

Diagnostic assays that use Qβ replicase to exponentially amplify a replicatable RNA reporter have many advantages: Qβ replicase is highly specific for its own template RNA (Haruna and Spiegelman, 1965c), and will not copy any other RNA in the sample. Amplification can be initiated with as little as one molecule of RNA (Levisohn and Spiegelman, 1968). Incubations are carried out at 37° C. and take less than 30 minutes; and the large amount of RNA that is synthesized (typically, 200 nanograms in a 50 microliter reaction) enables its detection by simple colorimetric methods. Quantitation of the number of targets originally present in a sample can occur over a range of target concentrations that exceeds 1,000,000-fold (Lizardi et al., 1988). The materials required for these assays are inexpensive, and the simplicity of the procedure lends itself to automation. Protocols that permit the simultaneous detection of cells infected with different pathogenic retroviruses in the same sample are effective with the recombinant RNA reporters of the subject invention.

SUMMARY OF THE INVENTION

The present invention concerns a replicatable and hybridizable recombinant single-stranded RNA probe molecule comprising: (a) a recognition sequence for the binding of an RNA-directed RNA polymerase; (b) a sequence required for the initiation of product strand synthesis by the polymerase; and (c) a heterologous RNA sequence inserted at a specific site in the internal region of the recombinant molecule and complementary to an oligo- or polynucleotide of interest.

The invention also provides a method for determining the presence or concentration of an oligo- or polynucleotide of interest in a sample, comprising the steps of: (a) forming a specific complex between the recombinant-RNA probe molecule described above and the oligo- or polynucleotide of interest, by incubating the sample with the recombinant-RNA probe molecules under suitable conditions and for a sufficient period of time to permit complementary nucleotide sequences to hybridize; (b) removing unhybridized recombinant-RNA probe molecules from the reaction mixture; (c)

incubating the reaction mixture with an RNA-directed RNA polymerase capable of synthesizing additional copies of the recombinant-RNA probe molecules that are hybridized to the oligo- or polynucleotide of interest; and (d) detecting the recombinant-RNA probe molecules synthesized in step (c), thereby determining the presence or concentration of the oligo- or polynucleotide of interest.

The invention herein further provides a method for simultaneously determining the presence or concentration of several different oligo- or polynucleotides of interest in a sample, comprising the steps of: (a) forming specific complexes between a mixture of different types of recombinant-RNA probe molecules described above, each type having a different inserted sequence, and the oligo- or polynucleotides of interest, by incubating the sample with the mixture of recombinant-RNA probe molecules under suitable conditions and for a sufficient period of time to permit complementary nucleotide sequences to hybridize; (b) removing unhybridized recombinant-RNA probe molecules from the reaction mixture; (c) incubating the reaction mixture with an RNA-directed RNA polymerase capable of synthesizing additional copies of the recombinant-RNA probe molecules which are hybridized to the oligo- or polynucleotides of interest; (d) separating the mixture of synthesized recombinant-RNAs by hybridizing them to an ordered array of polynucleotides bound to a solid support where each of the polynucleotides is complementary to one type of synthesized recombinant-RNA; and (e) detecting the recombinant-RNA probe molecules produced in step (d), thereby determining the presence or concentration of each oligo- or polynucleotide of interest.

BRIEF DESCRIPTION OF THE FIGURES

FIG. 1. Structure of plasmid pT7-MDV-poly. The heavy black line represents MDV-1 cDNA. When this plasmid is cleaved with endonuclease Sma I and incubated in vitro with T7 RNA polymerase, the resulting transcripts are replicatable RNAs.

FIG. 2. Nucleotide sequences of the recombinant transcripts folded into the secondary structures predicted by a computer program to be most stable (Zuker and Stiegler, 1981). MDV-fal-un (+) RNA 2(A) contains a 58-nucleotide insert (shown between the arrows) in place of the 3-nucleotide segment, AGU, that occurs in natural MDV-1 (+) RNA (Mills, et al. 1973). The secondary structures that the computer program predicts in the region of the recombinant outside the insert are identical to the secondary structures that were experimentally identified in MDV-1 RNA (Mills, et al. 1980; Kramer and Mills, 1981), suggesting that the probe sequence would have little effect on the topology of the MDV-1 domain. Bold letters indicate the nucleotides that are complementary to *P. falciparum* DNA. FIGS. 2(B) and 2(C) show the probable secondary structure of the inserts present in MDV-fal-st (+) RNA (B) and MDV-poly (+) RNA (C).

FIG. 3. Replication of recombinant RNAs. 3(A) Polyacrylamide gel electrophoresis showed the relative mobility of different transcripts: MDV-1 (a), MDV-poly (b), MDV-fal-un (c), and MDV-fal-st (d). The numbers on the side of the panel indicate the length of each transcript (in nucleotides). 3(B) Qβ replicase reactions were initiated with 200 fg of each transcript. Kinetic analysis showed that approximately 100,000 copies of each transcript were synthesized in 20 minutes. 3(C) Electrophoretic analysis of the RNA present after 45 minutes showed that the products were replicates of the transcripts. The products were probably one nucleotide longer than the transcripts, since a nonessential, 3'-terminal adenosine is usually added during replication (Bausch, et al. 1983).

FIG. 4. Effect of initial RNA concentration on the time-course of recombinant RNA synthesis. A series of 25 μl Qβ replicase reactions were initiated with the following quantities of MDV-fal-un RNA: 140 pg, 1.4 pg, 14 fg, 0.14 fg and 0 fg, which corresponds to $10^9$, $10^7$ $10^5$, $10^3$, and 0 molecules of added template. Samples of each reaction were taken every 5 minutes to determine the amount of RNA that had been synthesized. The results demonstrate that the time spent in the exponential phase of synthesis is increased when the initial number of template molecules is decreased (Kramer, et al. 1974). Each 100-fold reduction in the number of recombinant molecules used as template resulted in a 3.59 minute delay in achieving saturation (indicating that the RNA population doubled every 32.4 seconds). The electrophoretic mobility of the RNA present in each reaction after 25 minutes (see inset), compared with the mobility of recombinant RNA (278-nucleotides long) and MDV-1 RNA (223-nucleotides long) markers (m), confirmed that the product of reactions initiated with recombinant RNA was recombinant RNA.

FIG. 5. Hybridization of recombinant RNAs. 28 ng MDV-poly RNA (a), 75 ng MDV-fal-st RNA (b), and 75 ng MDV-fal-un RNA (c) were hybridized to dot-blots (34) containing either 0.5 μg pPFR6 DNA (a plasmid containing 45 copies of the *P. falciparum* target sequence) or 0.5 μg pUC13 DNA (the plasmid vector used to construct pPFR6). The recombinant RNA hybridized specifically to plasmids containing target sequences. When the amount of both the MDV-fal-un RNA and the DNA was doubled (d), a marked increase was seen in the amount of RNA that bound to the target DNA.

FIG. 6. Linear relationship between the logarithm of the initial number of RNA molecules added to a Qβ replicase reaction and the amount of product RNA synthesized. The amount of RNA synthesized in 25 minutes in the reactions shown in FIG. 4 was plotted against the logarithm of the number of recombinant molecules that had been added initially to each reaction. These results illustrate how bioassays that utilize replicatable probes would be interpreted: the amount of product RNA would be proportional to the logarithm of the number of probes bound to targets.

FIG. 7. Replicatable HIV-1 hybridization probe. The nucleotide sequence of MDV-hiv (+) RNA was folded into the secondary structures predicted to be most stable by a computer program. The probe sequence (bold letters) is located on the exterior of the molecule, where it is free to hybridize to its target, and where it is less likely to interfere with the sequences and structures required for replication.

FIG. 8. Schematic representation of the complex formed when a capture probe links a probe-target hybrid to an oligo(dT) group on the surface of a paramagnetic particle. The replicatable probe is a single-stranded RNA containing a probe sequence (thick line) embedded within the sequence of a replicatable RNA (indicated by the hairpin structures). The replicatable probe is joined by hydrogen bonds (cross-hatching) to its complementary target sequence within the target molecule. The target molecule can be an RNA or a DNA. The capture probe is a single-stranded DNA that contains a 5'-probe sequence that is hybridized to a different complementary target sequence within the target molecule. The target sequence for the capture probe is located relatively close to the target sequence for the replicatable probe on the target molecule. The capture probe also contains a 3'-poly(dA) tail that is hybridized to an oligo(dT) group on the surface of the paramagnetic particle. The hydrogen bonds that join the 3'-poly(dA) tail of the capture probe to the oligo(dT) group are relatively weak, permitting the much more stable probe-target hybrid to be released from the particle at higher guanidine thiocyanate concentrations.

Figure 9:
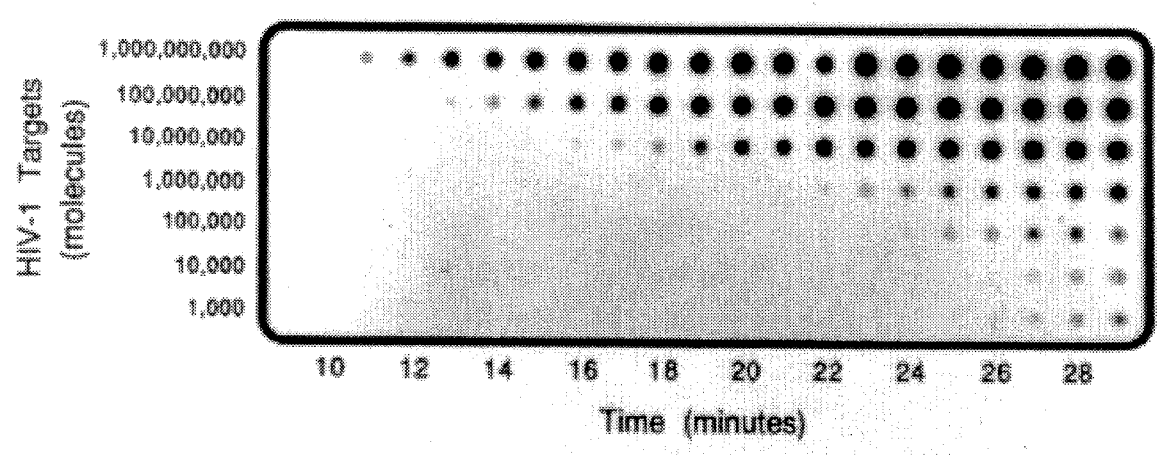

FIG. 9. Kinetic analysis of amplification reactions initiated with replicatable probes isolated from hybridization reactions. Approximately 50 ng of MDV-hiv RNA was synthesized in each amplification reaction. This amount of RNA is sufficient to have been accurately measured by the fluorescence of an intercalating dye, such as ethidium bromide.

DETAILED DESCRIPTION OF THE INVENTION

This invention concerns a replicatable and hybridizable recombinant single-stranded RNA probe molecule comprising (a) a recognition sequence for the binding of an RNA-directed RNA polymerase; (b) a sequence required for the initiation of product strand synthesis by the polymerase; and (c) a heterologous RNA sequence inserted at a specific site in the internal region of the recombinant molecule and complementary to an oligo- or polynucleotide of interest.

In one embodiment, the recognition sequence for the binding of an RNA-directed RNA polymerase is in an internal region of the recombinant-RNA probe molecule.

In another aspect of this invention, the insertion site for the heterologous RNA sequence is not near any sequence required for the binding of the RNA polymerase or for the initiation of product strand synthesis. In a further aspect, such an insert has a minimal affect on the replicability of the molecule. In a still yet further aspect of this invention, the insert in the recombinant-RNA probe molecule has a minimal effect upon the secondary and tertiary structure of the molecule. In the practice of this invention, the specific insertion site of the recombinant-RNA probe molecule is at a specific nucleotide.

The sequence in the recombinant RNA probe molecules of the present invention which is required for the initiation of product strand synthesis is a cytidine-rich 3'-terminal sequence.

An RNA-directed RNA polymerase useful in the practice of this invention is Qβ replicase.

Useful in the present invention is a recombinant-RNA probe molecule wherein the molecule is a variant RNA template for Qβ replicase or a mutant thereof. Examples of RNA variant templates for Qβ replicase are a microvariant RNA, a nanovariant RNA, cordycepin-tolerant RNA, or RQ120 RNA or a mutant thereof. In a further aspect, such a variant RNA template is MDV-1 RNA or a mutant thereof. In one embodiment, the MDV-1 RNA is MDV-1 (+) RNA. In another, the MDV-1 RNA is MDV-1(–) RNA. One feature of the invention herein is to provide a recombinant-RNA probe molecule wherein the heterologous sequence is inserted between nucleotides 63 and 64.

Transcripts derived from a recombinant plasmid by incubation with a DNA-directed RNA polymerase are especially useful in the practice of the invention to provide recombinant-RNA probe molecules. In the practice of this invention, the recombinant-RNA probe molecule is a variant RNA template for Qβ replicase or a mutant thereof. In a preferred embodiment, the variant RNA template is MDV-1 RNA or a mutant thereof, in particular, MDV-1 RNA wherein the heterologous sequence is inserted between nucleotides 63 and 64. In still other embodiments, the MDV-1 RNA is MDV-1 (+) RNA or MDV-1 (–) RNA.

An important feature is obtained by this invention where the inserted heterologous sequence of the recombinant-RNA probe molecule is complementary to a specific nucleic acid sequence of an infectious agent. Such an infectious agent may be a virus, a viroid or virusoid, a prokaryote such as a bacterium, a eukaryote such as a parasitic protozoan, for example a parasitic protozoan that causes malaria. Particular examples of viruses are HIV-1, HIV-2, HTLV-1, and HTLV-2, and an example of a specific nucleic acid sequence within any of these viruses is a highly conserved region in the viral pol gene.

In a further aspect, the inserted heterologous sequence of the recombinant-RNA probe molecule may be complementary to a specific gene sequence or portion thereof, or to an allele of the specific gene sequence or portion thereof.

The invention herein provides a method for determining the presence or concentration of an oligo- or polynucleotide of interest in a sample, comprising the steps of: (a) forming a specific complex between the recombinant-RNA probe molecules, as described above, and the oligo- or polynucleotide of interest, by incubating the sample with the recombinant-RNA probe molecules under suitable conditions and for a sufficient period of time to permit complementary nucleotide sequences to hybridize; (b) removing unhybridized recombinant-RNA probe molecules from the reaction mixture; (c) incubating the reaction mixture with an RNA-directed RNA polymerase capable of synthesizing additional copies of the recombinant-RNA probe molecules that are hybridized to the oligo- or polynucleotide of interest; and (d) detecting the recombinant-RNA probe molecules synthesized in step (c), thereby determining the presence or concentration of the oligo- or polynucleotide of interest.

Such a method as described above may be used to generate highly amplified signals in a nucleic acid hybridization assay. In theory the method has the power to generate a signal from a single hybridized molecule, and therefore, could be utilized to devise ultra-high sensitivity DNA (or RNA) detection assays. The method is based on the use of recombinant-RNA templates for Qβ replicase and Qβ replicase.

In such a method, the oligo- or polynucleotide in the sample may be bound to a solid support. In such cases, the solid support may be a nitrocellulose or nylon membrane.

In carrying out the above-described method of this invention and forming a specific complex between the recombinant-RNA probe molecules and the oligo- or polynucleotide of interest, i.e., step (a), the oligo- or polynucleotide of interest and the recombinant-RNA probe molecule may be in solution.

The unhybridized recombinant RNA molecules may be separated from those that are hybridized to the oligo- or polynucleotides of interest by employing techniques and skills which are well-known in the art. In the usual case, with the recombinant RNA molecule hybridized to the oligo- or polynucleotide of interest, which in turn is bound to a solid support, such separation is readily accomplished by simple washing which does not significantly disrupt the connection to the solid support. In addition, a technique known as the sandwich hybridization method may also be used to effect separation of hybridized from unhybridized recombinant-RNA molecules. Chromatographic and electrophoretic techniques may be uses as well. In a further aspect of the method described hereinabove, the unhybridized recombinant-RNA probe molecules are removed from the reaction mixture in step (b) by separating hybridized recombinant-RNA probe molecules from the unhybridized probe molecules through the capture of the oligo- or polynucleotide onto a solid support.

In a yet further aspect of this method, the hybridized recombinant-RNA probe molecules are separated from the unhybridized probe molecules by (a) capturing the oligo- or polynucleotide of interest onto a solid support comprising paramagnetic particles linked to oligo(dT) groups which are bound to the 3' poly(dA) tails of capture probes, the capture probes also comprising a sequence complementary to a sequence of the oligo- or polynucleotide of interest located close to the sequence of the oligo- or polynucleotide of interest that is specifically complexed to the recombinant-RNA probe molecule by hybridizing the oligo- or polynucleotide of interest to the complementary sequence of the capture probes, (b) placing the resulting reaction mixture in a magnetic field that draws the paramagnetic particles bound to the capture probe bound to the oligo- or polynucleotide of interest specifically complexed to the recombinant-RNA probe molecule to the walls of the container in which the reaction mixture is placed, and (c) withdrawing supernatant containing the unhybridized recombinant-RNA probe particles from the reaction mixture.

The magnetic beads may be minute iron oxide particles with extensively convoluted surfaces that are siliconized and contain a large number of covalently linked oligo(dT)$_{14}$ molecules. These beads are sold by Gene-Trak Systems of Framingham, Massachusetts. Probe-target hybrids are bound to these beads by means of capture probes, which are synthetic oligodeoxyribonucleotides, approximately 40 nucleotides in length, to which oligo (dA)$_{100-150}$ tails have been added by incubation with terminal transferase. The oligo(dA) tails enable capture probes to hybridize to the oligo(dT) on the surface of the beads, and the specific sequence at their other end enables them to hybridize to target strands at a location close to where the reporter probe binds. The following is an outline of a sample assay protocol: approximately $5 \times 10^6$ blood cells are lysed by incubation in 5M guanidine thiocyanate (GTC) for 2 minutes at 23° C. The lysate is diluted into a 120-µL hybridization mixture that contains $10^{11}$ recombinant-RNA reporter probes, $10^{11}$ capture probes, a large number of magnetic beads, and 2.5M GTC, which promotes hybridization. Hybridization takes about 60 minutes at 37° C. The magnetic beads, with the probe-target hybrids bound to their surface, are drawn to the walls of the reaction tube by placing the tube in the strong magnetic field of a magnetic separation device (Gene-Trak Systems). The hybridization solution is withdrawn by aspiration, and replaced by 250 µL of a fresh 2.5M GTC solution. The beads are then released from the walls of the tube by lifting the tube out of the magnetic field. The beads are washed by vortexing and pulled back to the walls of the tube. The solution is again removed by aspiration, but this time it will be replaced with a 3.25M GTC solution. The beads are again released and be incubated for 5 minutes at 37° C. In this more concentrated GTC solution, the relatively weak hybrids formed by the oligo(dA) tails of the capture probes and the oligo(dT)$_{14}$ on the surface of the beads come apart, releasing the much stronger target-probe hybrids back into solution. The stripped beads are drawn to the sides of the tube, and the released target-probe hybrids are transferred to a new tube containing new beads. The GTC concentration is then adjusted downwards to 2.5M, and the mixture incubated for 5 minutes at 37° C. to alow the target-probe hybrids to be recaptured onto the surface of the new beads.

In detecting the recombinant-RNA probe molecules which have been synthesized or replicated in step (c) above, methods well-known to those in this art may be employed. For example, detection can be by ultraviolet absorbance of replicated RNA, as, for example, by the method of contact photoprinting (Kutateladze, et al. 1979).

In one embodiment detecting is carried out by the incorporation of radioactively labelled ribonucleoside 5'-triphosphate precursors into the recombinant-RNA products. In another embodiment, detection is carried out by the incorporation of chemically modified ribonucleoside 5'-triphosphate precursors into the recombinant-RNA products.

Biotin or iminobiotin can be incorporated into replicated RNA, which can then be detected by known techniques with an enzyme-avidin or enzyme-streptavidin adduct, which binds to the RNA-bound biotin and catalyzes production of a conveniently detectable chromogen. See Matthews (Matthews, et al. 1985); Leary et al. (Leary, et al. 1983). Incorporation of biotin or iminobiotin into replicated RNA can be accomplished by employing UTP that is biotinylated through a spacer to carbon-5 of the uracil moiety as a substrate for the replicate in the replication reaction. Such UTP's are known compounds. Further, it is known that such UTP's are substrates for Qβ replicase, and that RNAs which include uracils biotinylated through spacer groups joined to the carbon-5 position, due to use of such UTP's in their synthesis, are templates for Qβ replicase catalyzed replication.

RNA resulting from the replication process could also be biotinylated employing photobiotin acetate according to the procedure of Forster, et al., (Forster, et al. 1985), and then detected, with an avidin-enzyme adduct-chromogenic compound system, like replicated RNA's synthesized with biotinylated UTP in the replication reaction. Thus, in still another aspect, the chemically modified ribonucleoside 5'-triphosphate precursors may be biotinylated or the chemically modified ribonucleotide 5'-triphosphate precursors may be fluorescent. A further feature of this method is obtained where detecting is carried out by the binding of RNA-specific chromogenic or fluorogenic dyes to the recombinant-RNA products. RNA resulting from the replication process can be made fluorescent by employing a T4 RNA ligase-catalyzed reaction to append nucleotides modified to be fluorescent to the 3'-end of replicative RNA. See Cosstick, et al., 1984. The fluorescence of the resulting RNA can be employed to detect the RNA by any of the several standard techniques.

Among still other methods that can be used to detect replicated RNA are those wherein a reporter substance, that binds specifically with nucleic acid, is added to the system in which the replication has taken place, or to the medium, such as a positively charged support such as ECTEOLA paper, on which replicated RNA has been isolated, and signal from the reporter substance measured. Such substances include: chromogenic dyes, such as "stains all" (Dahlberg, et al. 1969); methylene blue (Dingman and Peacock, 1968), and silver stain (Sammons, et al. 1981); Igloie, 1983); fluorogenic compounds that bind to RNA— for example, ethidium bromide (Sharp, et al., 1973; Bailey and Davidson, 1976); and fluorogenic compounds that bind specifically to RNAs that are templates for replication by Qβ replicase—for example, a phycobiliprotein (Oi, et al. 1982; Stryer, et al.; U.S. Pat. No. 4,520,110) conjugated to the viral subunit of Qβ replicase.

Detecting may be also carried out by physical methods, such as the absorption of ultraviolet light and the determination of mass by weighing.

In incubating the reaction mixture obtained in step (b), an RNA-directed RNA polymerase is employed. An example of such a polymerase useful in the practice of this invention is Qβ replicase.

A useful aspect of this invention is provided when the method described above is used to test a sample such as a tissue specimen, for example a blood specimen. A rapid and efficient assay is attained when the conditions for the hybridization step of the method comprise exposing the sample to guanidium thiocyanate. Guanidium thiocyanate prepares DNA from cells in the sample for hybridization in a single step, by simultaneously lysing the cells, denaturing nucleases, and unwinding the DNA from the cellular matrix.

This invention also provides recombinant-RNA probe molecules produced by the above-described method and, in particular, recombinant-RNA probe molecules produced by a method where the reaction mixture is incubated with Qβ replicase to synthesize additional copies of the recombinant-RNA probe molecules that are hybridized to the oligo- or polynucleotide of interest.

Another aspect of the method provided by this invention is attained when the time of incubation in step (c) is sufficiently short so that the number of recombinant-RNA product strands does not exceed the number of polymerase molecules, with the result that the number of recombinant-RNA product molecules is proportional to the logarithm of the number of recombinant-RNA probe molecules originally hybridized. The subject invention provides a method whereby the concentration of the oligo- or polynucleotide of interest detected in step (d) is measured by determining the intensity of a chromogenic or fluorescent signal in a reaction mixture in logarithmic phase at multiple time-points as the reaction proceeds and determining the concentration of the labelled recombinant-RNA products thereby, preparing a standard curve relating the concentration of the oligo- or polynucleotide of interest to the length of time of the reaction using a standard equation, and using the standard curve to determine the concentration of the oligo- or polynucleotide of interest at a known time point in the reaction. This method can be automated.

In more detail, during exponential synthesis, the time it takes for the RNA population to double is a constant for a given set of reaction conditions (Kramer, et al. 1974). If we know how many replicatable probes were initially present in a reaction, and if we know how long that reaction was incubated, then we can predict how many doublings have occurred and how many RNA molecules have been synthesized. Conversely, if we know how long it takes for a particular number of RNA molecules to be synthesized, then we can calculate how many molecules of replicatable probe were present initially. This relationship is summarized by the following equation:

$$N = N_0 2^{(t/d)}$$

where $N_0$ is the initial number of RNA molecules; t is the time of incubation; d is the characteristic time it takes for the RNA population to double; and N is the number of RNA molecules present at time t. Taking the logarithm of each side of the equation and then rearranging it algebraically:

$$\log N_0 = \frac{(-\log 2)}{d} t + \log N$$

where $(-\log 2)/d$ is a constant. If we determine the time it takes for each reaction to synthesize a particular number of RNA molecules, then log N will also be a constant and t will represent the time it takes for the RNA population to grow to N molecules. There will then be an inverse linear relationship between t and log $N_0$. Therefore, with a reliable method for determining the time it takes for an exponentially replicating RNA population to grow to a particular (though arbitrary) number of molecules, we can accurately determine the initial number of replicatable probes. A useful method for determining how long it takes for a particular number of RNA molecules to be synthesized is as follows: An intercalating fluorescent dye, such as ethidium bromide, is included in the RNA amplification reaction mixture. An ethidium bromide concentration of about 1 μmol/L gives a good signal, without significantly inhibiting replication (Kramer, et al. 1988). Ethidium bromide becomes fluorescent when it interacts with secondary structures present in replicatable probes. A simple instrument periodically monitors the fluorescence of the ethidium bromide in an entire set of amplification reactions. Initially, the number of RNA molecules is too low to produce an appreciable fluorescence. However, as exponential synthesis proceeds, the fluorescence increases. The instrument is programmed to store the kinetic data and to use this data to determine the time for each reaction at which the fluorescence corresponds to the presence of a particular number of RNA molecules (the "endpoint"). The inclusion of standards in the hybridization reaction, each containing a known number of target molecules, permits the establishment of a "standard curve", in which the logarithm of the number of target molecules is inversely proportional to the time at which the endpoint is reached (as described in the second equation). The number of target molecules in each of the unknown samples is then determined by comparing their endpoints with those on the standard curve. This method is readily automatable; it does not require radioactive compounds; the magnitude of the fluorescent signal at the endpoint is the same for all the reactions, and is well above fluorescent background; the assay is accurate; and the logarithmic nature of the standard curve permits the determination of the number of targets in a sample over an extremely wide range of target concentrations.

The method described herein provides another important feature where the time of incubation in step (c) is sufficiently long so that the number of recombinant-RNA product strands exceeds the number of polymerase molecules, with the result that the number of recombinant-RNA product molecules is linearly proportional to the number of recombinant-RNA probe molecules originally hybridized. The subject invention provides a method whereby the concentration of the oligo- or polynucleotide of interest detected in step (d) is determined by preparing standards containing a known amount of recombinant-RNA probe molecules and directly relating the amount of recombinant-RNA product strands present in the hybridization reaction at a given time in the linear phase of the hybridization reaction to the logarithm of the number of recombinant-RNA probe molecules originally hybridized by using the known standards prepared as described.

In a clinical setting, in which the assays would be automated, it is preferable to detect the synthesized RNA by the fluorescence that occurs when ethidium bromide binds to RNA. Since these assays are incubated long enough for the replicase to become saturated with RNA, the amount of RNA synthesized by the end of the incubation period is directly proportional to the logarithm of the number of target sequences that were present in the original sample (Lizardi, et al., 1988). The inclusion of samples containing known standards, along with the unknown samples to be assayed, permits the direct determination of the number of molecular targets that were present in each sample. An example of this method for analyzing the data is as follows: Once the saturation point is reached in an amplification reaction, the number of RNA molecules increases linearly with time. For example reactions that have been incubated for at least 28 min, have generally passed the saturation point and reached the linear phase of synthesis. A comparison of the amounts of RNA present in each sample at 28 minutes shows that the most RNA is present in those samples that correspond to the hybridization reactions that contained the most targets. Because these reactions were initiated with the greatest number of replicatable probes, they reached the saturation point soonest and had the longest period of time to synthesize RNA in the linear phase. We can analyze the data by using the direct linear relationship between the amount of RNA present at a particular (though arbitrary) time in the linear phase and the logarithm of the number of replicatable probes that initiate a reaction (Lizardi, et al. 1988). Known standards are included among the unknown samples to be tested, and used to determine the number of target molecules present in each unknown sample. Because it is relatively simple to devise an assay kit to measure the amount of RNA synthesized in a reaction that is incubated for a fixed length of time, this alternative analytical approach is an inexpensive method for detecting infectious agents in the field.

This invention also provides a method for simultaneously determining the presence or concentration of several different oligo- or polynucleotides of interest in a sample, comprising the steps of: (a) forming specific complexes between a mixture of different types of recombinant-RNA probe molecules described above comprising a recognition sequence for the binding of an RNA-directed RNA polymerase, a sequence required for the initiation of product strand synthesis by the polymerase, and a heterologous RNA sequence inserted at a specific site in the internal region of the recombinant molecule and complementary to an oligo- or polynucleotide of interest, each type having a different inserted sequence, and the oligo- or polynucleotides of interest, by incubating the sample with the mixture of recombinant-RNA probe molecules under suitable conditions and for a sufficient period of time to permit complementary nucleotide sequences to hybridize; (b) removing unhybridized recombinant-RNA probe molecules from the reaction mixture; (c) incubating the reaction mixture with an RNA-directed RNA polymerase capable of synthesizing additional copies of the recombinant-RNA probe molecules that are hybridized to the oligo- or polynucleotides of interest; (d) separating the mixture of synthesized recombinant-RNAs by hybridizing them to an ordered array of polynucleotides bound to a solid support, where each of the polynucleotides is complementary to one type of synthesized recombinant-RNA; and (e) detecting the recombinant-RNA probe molecules produced in step (d), thereby determining the presence or concentration of each oligo- or polynucleotide of interest. A useful aspect of this invention is provided when the sample is a tissue specimen, such as a blood sample. A particularly efficient method is provided when the conditions for hybridization comprise exposing the sample to guanidine thiocyanate. The solid support provided may be a membrane, for example a nitrocellulose or nylon membrane.

A good clinical assay requires speed, specificity and sensitivity. For example, current assays for the identification of the pathogenic agents that cause acute bacterial meningitis lack sufficient speed and sensitivity. A number of different organisms are associated with meningitis, including *Haemophilus influenza*, *Klebsiella pneumonia*, *Neisseria menigitidis*, *Staphylococcus aureus*, and *Streptococcus pneumonia*. The patient is typically a young child. Effective treatment requires the identification of the etiologic agent in a sample of cerebrospinal fluid; and it is essential that antibiotic treatment begin as soon as possible. However, current laboratory techniques require at least 18 hours to identify the agent. Moreover, the sample volume is usually only 50 microliters and often contains less than 50 individual microorganisms, which is well below the limits at which reliable direct detection assays can currently be carried out. The clinical picture is further complicated by a marked increase in the abundance of bacteria that possess antibiotic resistance genes on plasmids.

A series of replicatable recombinant-RNA probes molecules can be prepared each of which is specific for a different organism that can cause meningitis. In addition, a series of recombinant-RNA probe molecules can be prepared, each of which is specific for different antibiotic resistance genes that could be present in the infectious agent.

Using such a series of recombinant-RNA probe molecules a mixture of, for example, 15 different replicatable recombinant-RNA probes are incubated with denatured DNA obtained from a sample of spinal fluid. Only a few types of recombinant-RNA probe molecules species will find targets (for example, one bacterial probe and three resistance gene probes). After removing the unbound probe molecules, Qβ replicase is used to amplify the remaining probes. After amplification, the mixture of product RNAs is placed in contact with a membrane containing numbered dot-blots, each of which contains denatured DNA complementary to one of the original probe sequences. In this manner, the mixture of product RNAs is sorted out for subsequent quantification. These assays permit the rapid and simultaneous diagnosis of both the pathogenic agent and its spectrum of antibiotic resistance.

In a similar manner a mixture of probes could be used simultaneously to detect the human immunodeficiency virus which causes acquired immune deficiency syndrome (AIDS) and the concentration of an entire panel of opportunistic agents that infect the immunosuppressed patient.

This invention is illustrated in the Experimental Details and Experimental Discussion sections which follow. These sections are set forth to aid in an understanding of the invention but are not intended to, and should not be constructed to, limit in any way the invention as set forth in the claims which follow thereafter.

EXPERIMENTAL DETAILS

EXAMPLE 1

Materials and Methods

Enzymes

Restriction endonucleases, T4 polynucleotide kinase, and T7 RNA polymerase were purchased from New England Biolabs. Calf intestine alkaline phosphatase, T4 DNA ligase, the Klenow fragment of *Escherichia coli* DNA polymerase I, and bovine pancreatic deoxyribonuclease I were purchased from Boehringer Mannheim. Qβ replicase was isolated from bacteriophage Qβ-infected *E. coli* Q13 by the procedure of Eoyang and August (17), with the hydroxyapatite step omitted.

Oligonucleotides

Single-stranded DNA fragments were prepared, using β-cyanoethyl phosphoramidite chemistry (Gait, 1984), in a Microsyn-1450A synthesized (Systec). After deblocking and release from the resin, the oligonucleotides were isolated by preparative gel electrophoresis (Matthes, et al. 1984), eluted from the gel, filtered through nitrocellulose, and purified by chromatography (Lo, et al. 1984) on SEP-PAK C18 cartridges (Waters Associates).

Plasmid for Synthesizing MDV-1(+) RNA by Transcription pT7-MDV contains a promoter for T7 RNA polymerase directed towards a full-length cDNA prepared from MDV-1 RNA (Mills, et al. 1988). This plasmid had been constructed so that transcription from the T7 promoter begins with the first nucleotide of MDV-1 (+) RNA. A Sma I restriction site had been introduced at the other end of the MDV-1 cDNA sequence so that when this plasmid is linearized by digestion with endonuclease Sma I and then incubated with T7 RNA polymerase, transcription terminates two nucleotides before the end of MDV-1 (+) RNA. The resulting transcripts, lacking the natural 3'-terminal dinucleotide CpA-OH, serve as excellent templates for exponential replication by Qβ replicase (Mills, et al. 1988).

Plasmid Containing a Polylinker within the MDV-1 cDNA Sequence

The PpuM I-BstE II fragment of the MDV-1 cDNA sequence in pT7-MDV DNA was replaced with the corresponding PpuM I-BstE II fragment of a modified MDV-1 cDNA that contained a unique Xba I recognition sequence in place of the only Hinf I recognition sequence in MDV-1 cDNA (Bausch, et al. 1983). A synthetic DNA fragment (prepared by annealing dCTAGATCTCGAGGCCTG to dCTAGCAGGCCTCGAGAT) was then cloned into this Xba I site, converting it into a polylinker possessing unique restriction sites for Xba I, Bgl II, Xho I, and Stu I. This plasmid, designated pT7-MDV-poly, is diagrammed in FIG. 1. The RNA synthesized from this plasmid is designated MDV-poly. Recombinant RNAs can be generated by inserting any heterologous DNA sequence into one of the unique restriction sites in the polylinker of pT7-MDV-poly, and then utilizing the resulting plasmid as a template for transcription by T7 RNA polymerase.

Plasmids for Synthesizing Recombinant Probes by Transcription pT7-MDV-fal-un was constructed by inserting a synthetic probe sequence (prepared by annealing dTCGAGACTAACATAGGTCTTAACTTGACTAACA to dTCGATGTTAGTCAAGT TAAGACCTATGTTAGTC) into the Xho I site of the polylinker sequence in pT7-MDV-poly. pT7-MDV-fal-st was constructed by inserting the related synthetic probe sequence (prepared by annealing dTCGAGACTAACATAGG TCTAACTTGTTAGTCA to dTCGATGACTAACAAGTTAAGACCTATGTTAGTC) into the site in pT7-MDV-poly. Both probe sequences were complementary to the unique 21-base-pair sequences motif that is repeated over 1,000 times in *P. falciparum* DNA (Franzen, et al. 1984; Aslund, et al 1985; Zolg, et al. 1987). The specific sequence used herein was determined by sequencing cloned repetitive DNA isolated from strain FCR-3/Gambia.

Nucleotide Sequence Analysis

The nucleotide sequence in the recombinant region of each plasmid was determined by the chain termination procedure (Sanger, et al. 1977), utilizing 7-deaza-deoxyguanosine 5'-triphosphate (Boehringer Mannheim) in place of deoxyguanosine 5'-triphosphate (Mizusawa, et al. 1986), and [$^{35}$S]deoxycytidine 5'(a-thio) triphosphate (New England Nuclear) as label (Biggin, et al. 1983). Sequencing reactions were carried out on total plasmid DNA (Wallace, et al. 1981), utilizing a 20-nucleotide primer (Pharmacia) that was complementary to the T7 promoter sequence (Osterman and Coleman, 1981).

Transcription

Plasmids were isolated from bacteria by the method of Holmes and Quigley (Holmes and Quigley, 1981) and purified by gel filtration chromatography (Bywater, et al. 1983) on Sephacryl S-1000 (Pharmacia). Plasmid DNA was then digested with Sma I or Stu I. Transcription was carried out according to a modification Of the protocol of Axelrod and Kramer (Axelrod and Kramer, 1985): 1 μg of linearized DNA was incubated with 80 units of T7 RNA polymerase for 3 hr at 37° C. in 40 μl of 400 μM ATP, 400 μM [α-$^{32}$P] CTP, 400 μM GTP, 400 μM UTP, 50 mM Tris-HCl (ph 8.0), 12 mM $MgCl_2$, 5 mM dithiothreitol (freshly prepared), 100 μg/ml bovine serum albumin, 4 mM spermidine, and 1 unit/μl of the ribonuclease inhibitor, RNasin (Promega Biotec). The [$^{32}$P] transcripts were incubated with 0.1 μg/μl of ribonuclease-free deoxyribonuclease I (Tullis and Rubin, 1980) to destroy the template DNA, and then purified by phenol/chloroform/isoamyl alcohol extraction, followed by precipitation with ethanol. The concentration of each RNA was determined from its specific radioactivity. The size and homogeneity of the RNA was determined by electrophoresis through 6% polyacrylamide slab gels in the presence of 7M urea (Maniatis and van deSande, 1975). The RNA bands were visualized by silver staining (Sammons, et al. 1981).

Replication

Between $1.4\times10^{-18}$ g and $1.4\times10^{-10}$ of transcripts (depending on the reaction) were incubated with $2.4\times10^{-6}$ g of Qβ replicase at 37° C. in 25 μl of 400 μM ATP, 400 μM [α-$^{32}$P]CTP, 400 μM GTP, 400 μM UTP, 14 mM $MgCl_2$, and 90 mM Tris-HCl (pH 7.5). Each reaction was sampled every 5 min. The amount of RNA in each 2-μl sample was determined by binding the [$^{32}$ P]RNA to DE81 cellulose discs (Whatman), as described by Maxwell and his coworkers (Maxwell, et al. 1978), and measuring the radioactivity on each disc with a scintillation counter. The size and homogeneity of the RNA in selected samples was determined by polyacrylamide gel electrophoresis. The [$^{32}$P] RNA bands were detected by autoradiography.

Hybridization

Two different plasmids were used as targets. The first, pPFR6, was constructed by the insertion of a DNA fragment containing 45 tandem copies of the 21 base-pair repetitive sequence of *P. falciparum* DNA (strain FCR-3/Gambia) into the BamH I site of pUC13 DNA (Boehringer Mannheim). Fifteen of the 45 repeated sequences were identical to the inserted sequence in the recombinant RNA probes. The other repeated sequences contained microheterogeneities. The second plasmid, pUC13, served as a negative control for hybridization of the recombinant RNA probes. Each plasmid was linearized by digestion with BamH I, denatured by incubation in 0.4 NaOH for 60 sec at 42° C., and 0.5-μg or 1.0-μg aliquots were bound to a BA83 nitrocellulose membrane (Schleicher and Schuell), according to the dot-blot procedure of Kafatos and his coworkers (Kafatos, et al. 1979). The membrane was cut into sections, each containing a duplicate pair of pPFR6 and pUC13 dot-blots. Each membrane section was prehybridized for 3 hr at 37° C. in 5X SSPE (5X SSPE is 900 mM NaCl, 50 mM sodium phosphate (pH 7.4), and 5 mM EDTA), 2 mg/ml sodium dodecyl sulfate, 500 μg/ml heparin (Sigma), and 20% formamide. Each membrane section was then incubated for 4 hrs at 25° C. with between 23 ng and 150 ng of the [$^{32}$P]RNA to be tested and 10 μg of unlabeled *E. coli* tRNA carrier (Boehringer Mannheim) dissolved in 2 ml of the prehybridization buffer. The following RNAs were tested: MDV-poly, MDV-fal-un, MDV-fal-st, and truncated versions of each (transcribed from plasmids cleaved at the Stu I site). After hybridization, the membranes were washed three times (15 min/wash) at 25° C. with a solution containing 4X SSPE, 2 mg/ml sodium dodecyl sulfate, and 400 μg/ml heparin, followed by two 10-min washes at 25° C. in 1X SSPE, and a 12-min wash at 37 C in 1X SSPE. The hybridized RNA was detected by autoradiography.

Replication of Recombinant RNAs after Hybridization

To study the replicability of bound RNA, MDV-fal-un RNA hybridized to dot-blots was eluted by boiling in 200 µl of water for 60 sec. The integrity of the eluted RNA was analyzed by polyacrylamide gel electrophoresis. The replicability of the eluted RNA was determined by initiating a Qβ replicase reaction with 0.1 µl of the eluant. This reaction was followed kinetically, and the identity of the product RNA was determined by polyacrylamide gel electrophoresis. In addition, individual hybridized dot-blots were added directly to Qβ replicase reactions to see whether bound RNA could serve as a template. These reactions contained 100 µg/ml bovine serum albumin to preclude the possibility that Qβ replicase would bind to the nitrocellulose membrane.

Experimental Results

Design of the Replicatable Probes

Figure 2A:
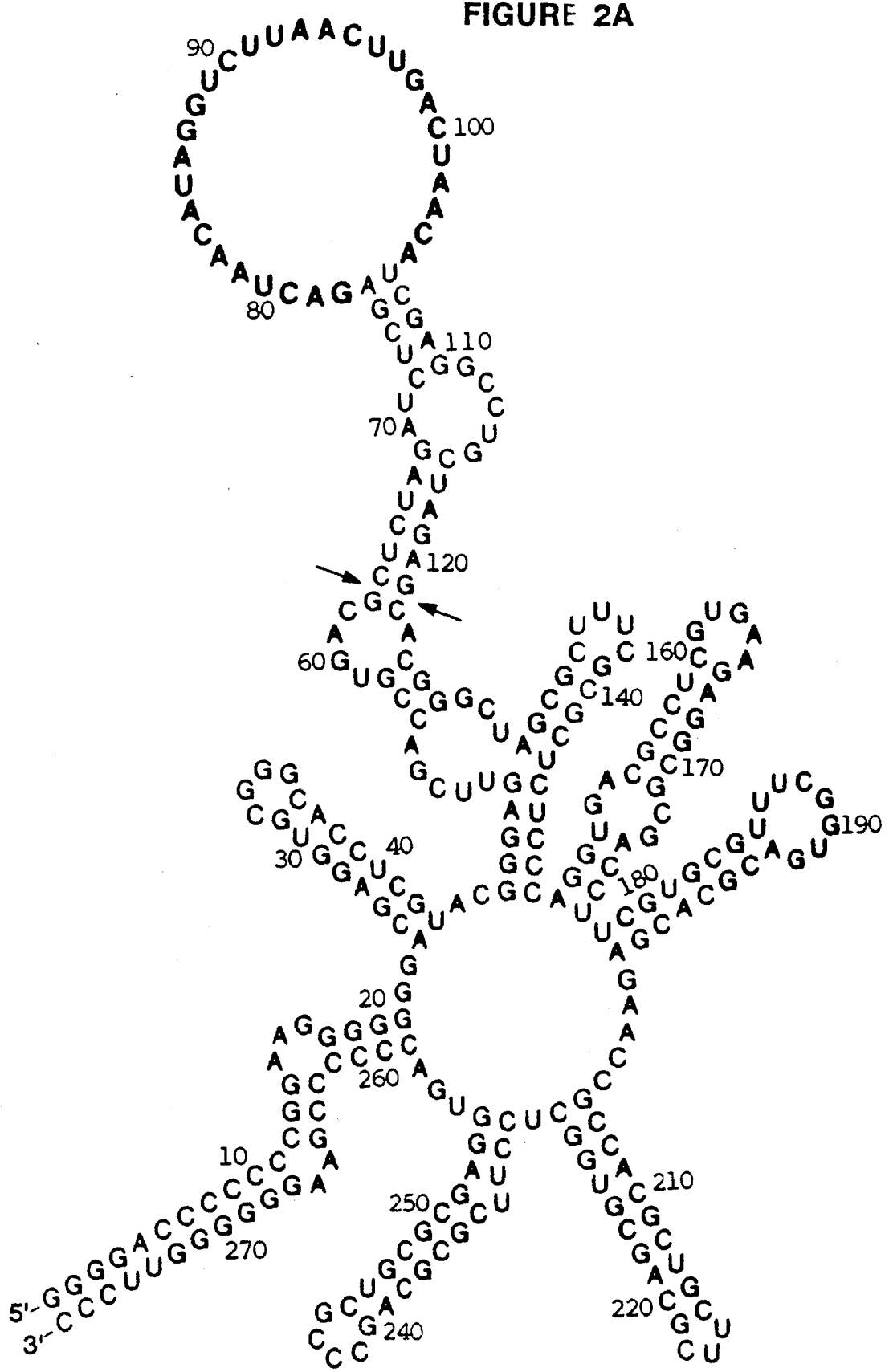
Figure 2B:
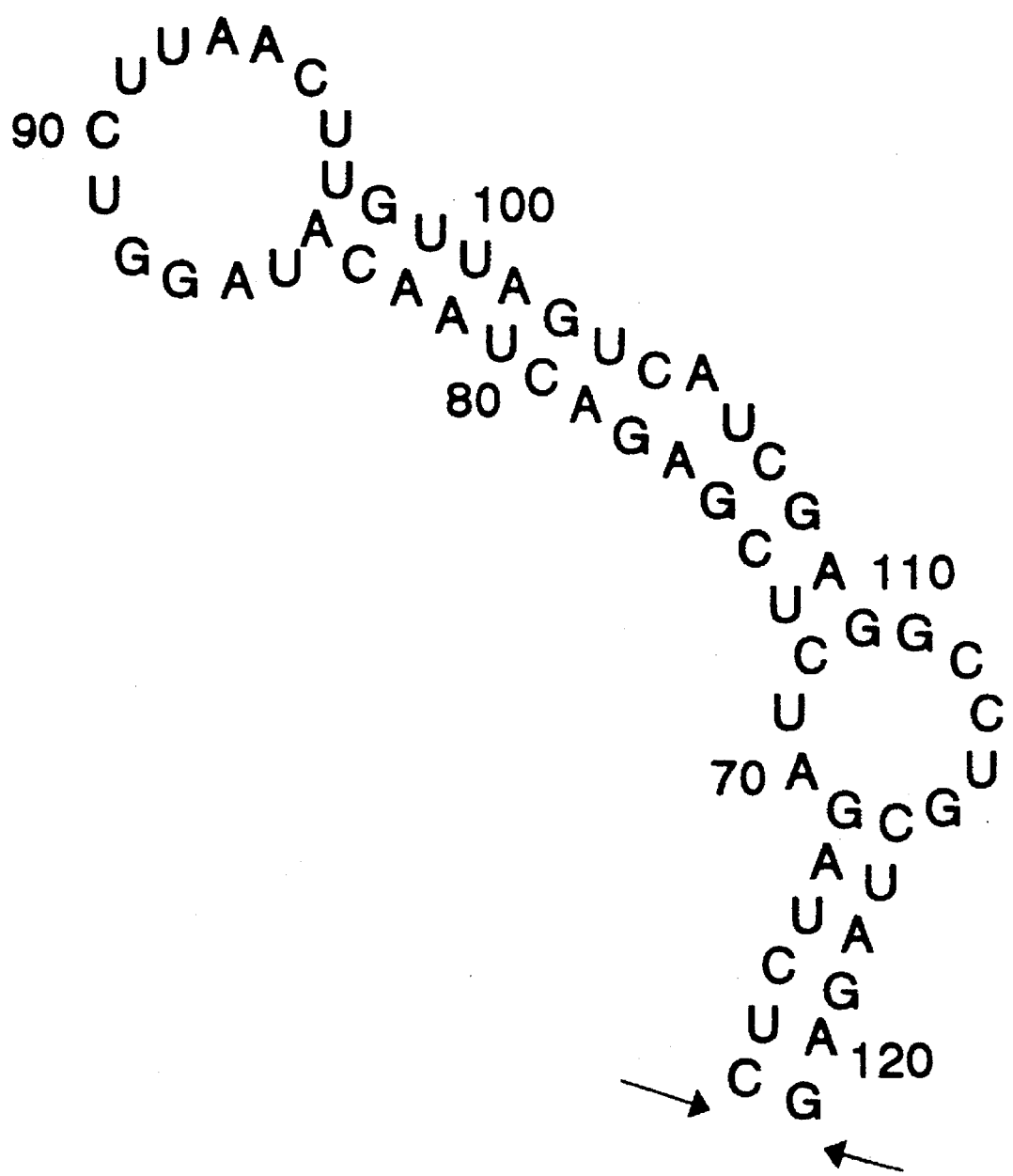
Figure 2C:
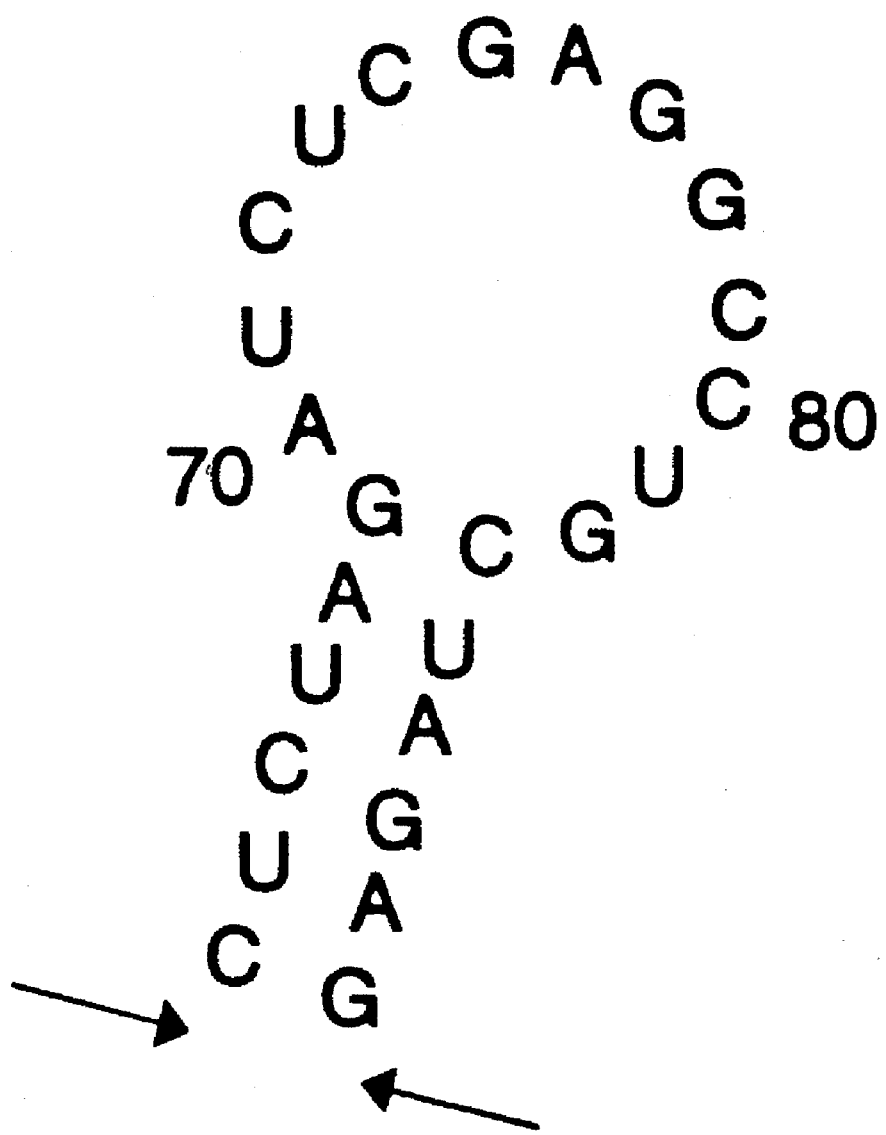

One of the goals of the present invention was to construct an RNA that would serve both as a specific probe for *P. falciparum* DNA and as a template for exponential amplification by Qβ replicase. MDV-1 RNA was chosen as the parent molecule because modified MDV-1 RNAs can be synthesized by transcription from recombinant plasmids (Mills, et al. 1988). MDV-1 RNA contains many stable secondary structures (Klotz, et al. 1980; Mills, et al. 1980; Kramer and Mills, 1981), and these secondary structures are required for replication (Mills, et al. 1978; Nishihara, et al. 1983; Priano, et al. 1987). The site which was chosen for inserting probe sequences into MDV-1 RNA was located on the exterior of the molecule (Miele, et al. 1972), where the insert was less likely to disturb the structure, and therefore less likely to interfere with replication. In selecting the sequence of the probe two main concerns had to be reconciled: 1) the inserted sequence might have to assume a single-stranded conformation for it to hybridize to its target sequence; and 2) the inserted sequence might have to form secondary structures, otherwise the product and the template might form a lethal duplex during replication (Priano, et al. 1987). Because these two concerns imposed contradictory constraints on the design of the inserted sequence, two recombinant RNAs were prepared each containing a different probe sequence. The first recombinant, MDV-fal-un RNA, was likely to possess an unstructured probe region, according to a computer analysis of its sequence (Zuker and Stiegler, 1981). The second recombinant, MDV-fal-st RNA, differed from MDV-fal-un RNA in a 5-nucleotide region. As a consequence, it was likely to form a more stable secondary structure in the region containing the probe. FIG. 2 shows the nucleotide sequence and probable secondary structure (Zuker and Stiegler, 1981) of MDV-fal-un RNA, MDV-fal-st RNA, and MDV-poly RNA.

Replication of the Recombinant RNAs

Figure 3A:
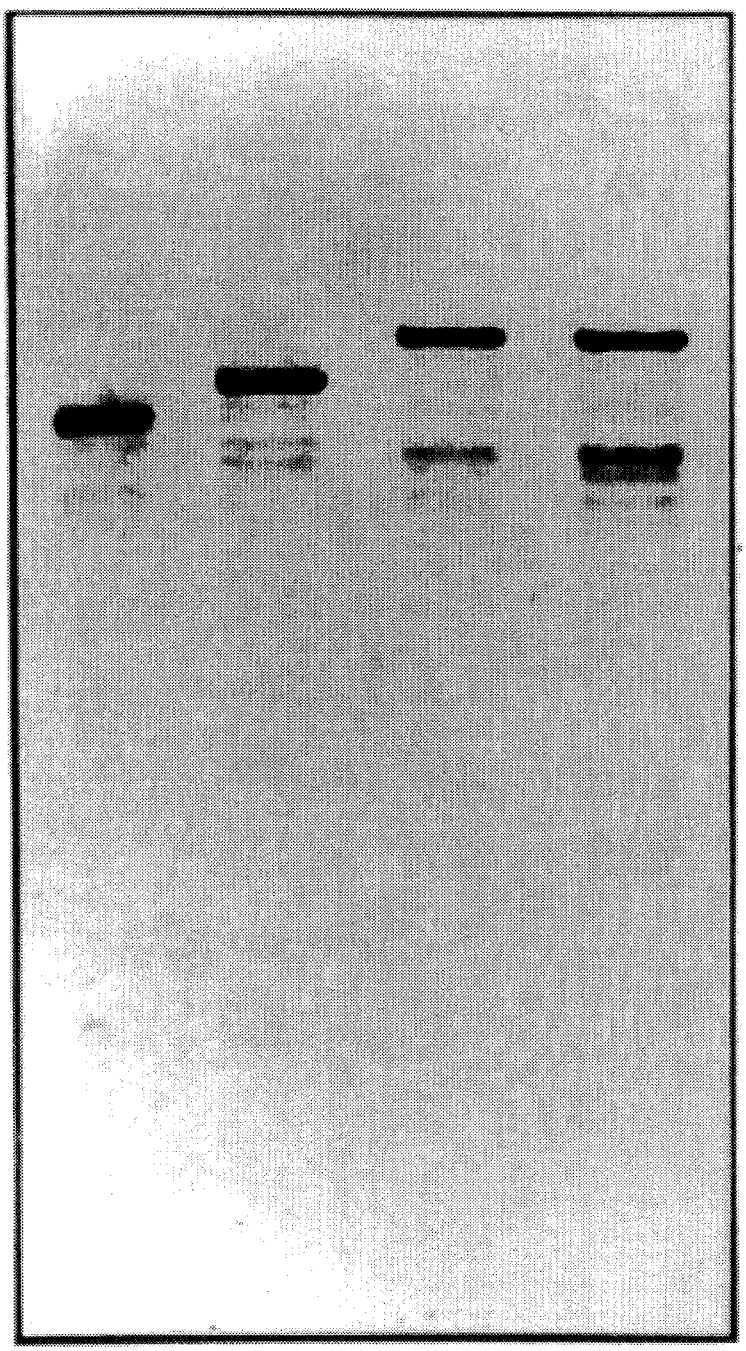
Figure 3B:
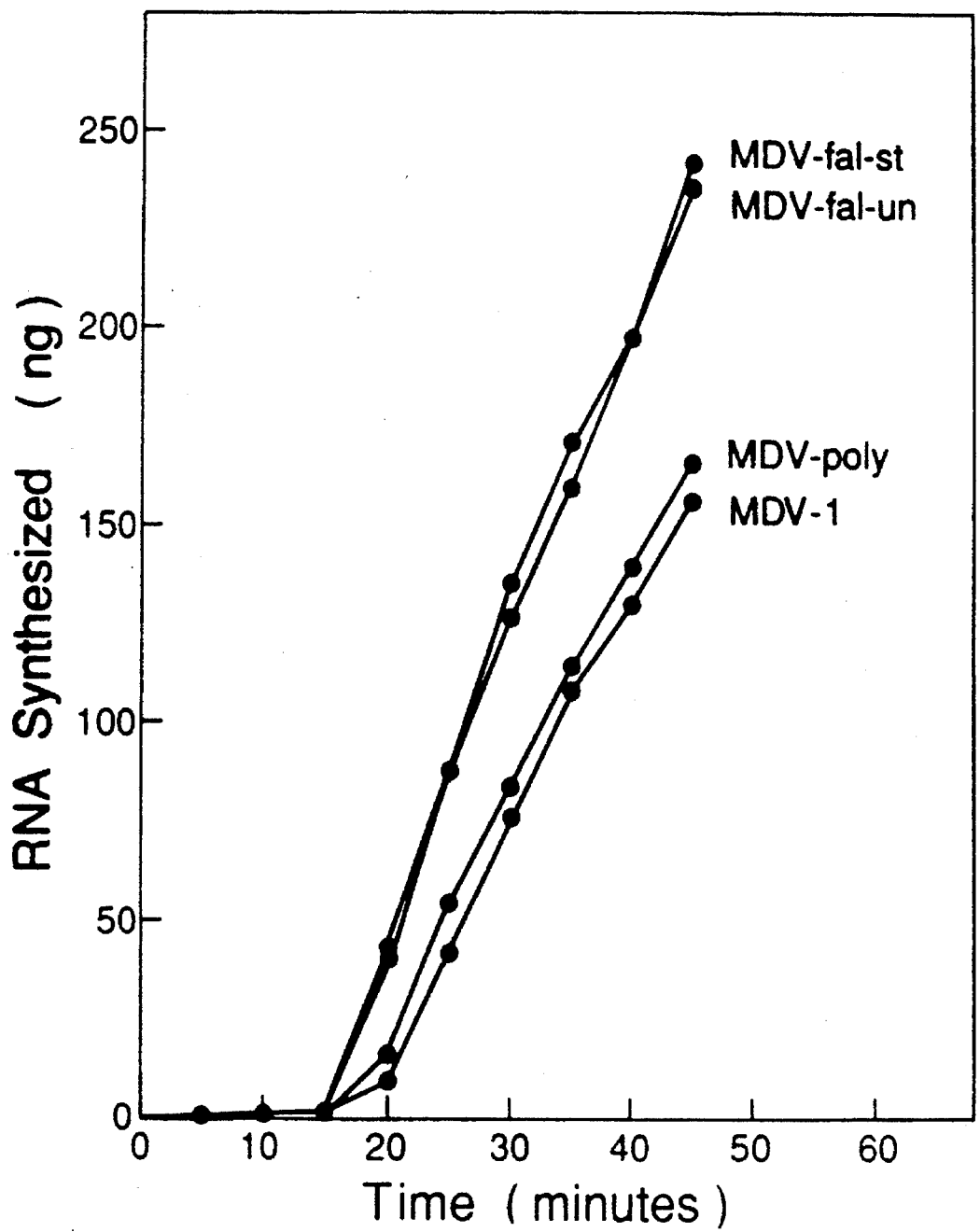
Figure 3C:
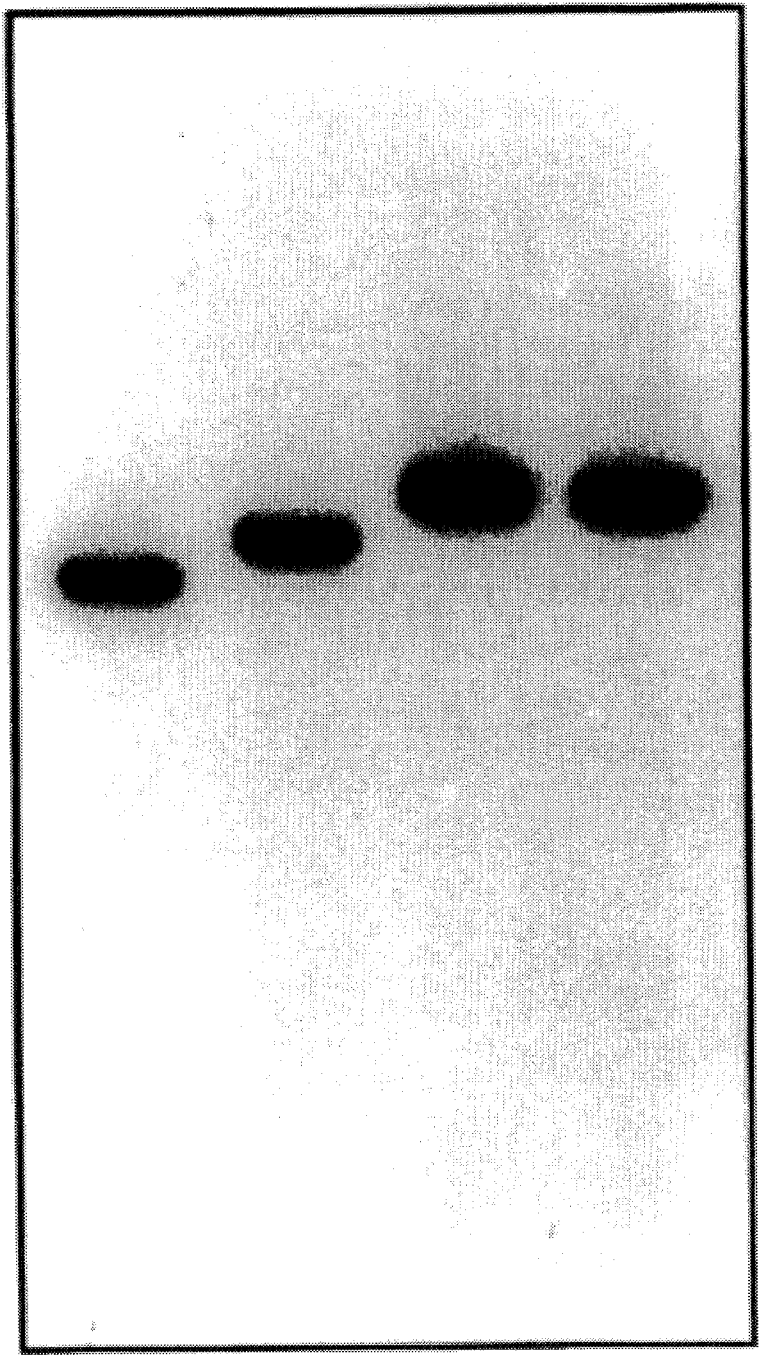

Four different RNAs were prepared by transcription in vitro: MDV-1, MDV-poly, MDV-fal-un, and MDV-fal-st. Electrophoretic analysis of these transcripts, as illustrated in FIG. 3(A), demonstrated that the recombinants that contained probe sequences could easily be distinguished from the other transcripts by their relative mobility. The transcripts were then isolated from the reaction mixture and used as templates for the synthesis of additional RNA by Qβ replicase. Kinetic analysis of the amount of RNA synthesized in the Qβ replicase reactions, as shown in FIG. 3(B), demonstrated that both the structured and the unstructured recombinant RNAs were excellent templates for exponential replication. Furthermore, as shown in FIG. 3(C), electrophoretic analysis of the RNA synthesized in each Qβ replicase reaction, showed that the products were homogenous replicates of the original transcripts.

To compare the rate of replication of recombinant RNA to the rate of replication of MDV-1 RNA, Qβ replicase reactions were initiated with mixtures of MDV-fal-st (+) RNA and MDV-1 (+) RNA. The reactions were incubated for 20 minutes, permitting the synthesis of approximately ten million copies of each RNA. The RNA products of the reactions were analyzed by polyacrylamide gel electrophoresis. The results are shown in Table 1 and indicate that, despite recombinant RNA being 55 nucleotides longer than the MDV-1 RNA from which it was derived, it is amplified at essentially the same rate by Qβ replicase.

TABLE 1

| Replication of Mixtures of MDV-1 RNA and Recombinant RNA | | | |
|---|---|---|---|
| Initial RNA (fg) | | Product RNA (ng) | |
| MDV-1 | MDV-fal-st | MDV-1 | MDV-fal-st |
| 1 | 1 | 42 | 54 |
| 10 | 1 | 115 | 13 |
| 1 | 10 | 17 | 149 |

Exponential Amplification after Serial Dilution

Because the sensitivity of bioassays employing replicatable probes will depend on how few recombinant molecules can serve as templates for the synthesis of an easily detectable quantity of product RNA, a series of Qβ replicase reactions were initiated with decreasing amounts of MDV-fal-un RNA. The results of these series of reactions are shown in FIG. 4 and demonstrate that a reaction initiated with as few as 1,000 molecules of recombinant RNA (0.14 fg) produced 129 nanograms of recombinant RNA product after 30 minutes of synthesis, which is a one-billion-fold amplification. Virtually identical kinetic results were obtained in a parallel series of reactions initiated with MDV-fal-st RNA, indicating that the relative lack of secondary structure in the probe region of MDV-fal-un RNA had no discernible effect on replication.

Electrophoretic analysis showed that the product of the reaction to which no exogenous template had been added was MDV-1 RNA. This analysis is illustrated in the inset of FIG. 4. This was expected, because the method which was used for isolating Qβ replicase (Eoyang and August, 1971) does not eliminate all of the contaminating MDV-1 RNA molecules (Kramer, et al. 1974). Based on the time it took for this reaction to achieve saturation (when the number of RNA molecules equals the number of active replicase molecules), it is calculated that only 40 molecules of MDV-1 RNA were present initially. This was confirmed by the following results: when a reaction was initiated with 100 molecules of MDV-fal-un RNA, the 25-minute product contained 30% MDV-1 RNA; and a reaction initiated with only 10 molecules of MDV-fal-un RNA contained mostly MDV-1RNA. Had Qβ replicase that had been freed of all contaminating RNA (Hill and Blumenthal, 1983), been used instead, it would have been expected that only recombinant RNA would have been synthesized.

Hybridization of the Recombinant RNAs

Each of the recombinant RNAs was shown to bind specifically to denatured plasmids containing a known quantity of *P. falciparum* target sequences (FIG. 5). Neither recombinant RNA bound to control plasmids that lacked *P. falciparum* sequences. Furthermore, MDV-poly RNA, which does not contain a probe sequence, did not bind to either plasmid. Taken together, these results demonstrate that both recombinant RNAs bind specifically to their targets and that, under the hybridization conditions employed, the presence of structure in the probe region has little effect on hybridization.

In another experiment, truncated versions of each recombinant probe were prepared by transcription from plasmids that had been linearized by digestion with Stu 1, instead of Sma I. These transcripts were 111-nucleotides long, and contained 63 nucleotides from the 5' end of MDV-1 (+) RNA and 48 nucleotides from the insert region, including the entire probe sequence. Under the hybridization conditions employed, no difference could be observed between the hybridization of the truncated RNAs and the hybridization of the full-length RNAs. This result demonstrates that the constrained topology of the MDV-1 domain (Sammmons, et al. 1981) that surrounds the probe region in the full-length molecule has little effect on the ability of the probe to hybridize to its target.

Replication of Recombinant RNAs after Hybridization

Additional experiments were carried out to determine whether hybridized recombinant RNAs retain their ability to serve as templates for Qβ replicase after all the manipulations that occur during filter hybridization. MDV-fal-un RNA that had been hybridized to plasmids containing *P. falciparum* sequences was eluted from the dot-blot by a brief heating step. Electrophoretic analysis of this RNA showed that intact recombinant molecules had been released. A portion of the eluted RNA was then tested to see whether it could serve as a template for Qβ replicase. A ten-million-fold amplification occurred in 20 minutes. Electrophoretic analysis of the product of this reaction showed that it was pure MDV-fal-un RNA. From the results of these experiments it was estimated that at least 10 percent of the eluted RNA had retained its biological activity.

Another experiment was performed to see whether recombinant probes could serve as templates for Qβ replicase while still bound to dot-blots. Membrane fragments containing hybridized MDV-fal-un RNA were incubated directly with Qβ replicase. Reactions containing membranes with RNA hybridized to target sequences synthesized more recombinant RNA than reactions containing membranes that lacked target sequences. These preliminary results suggest that a special release step may not be necessary to initiate the replication of hybridized recombinant RNAs.

Experimental Discussion

Figure 4:
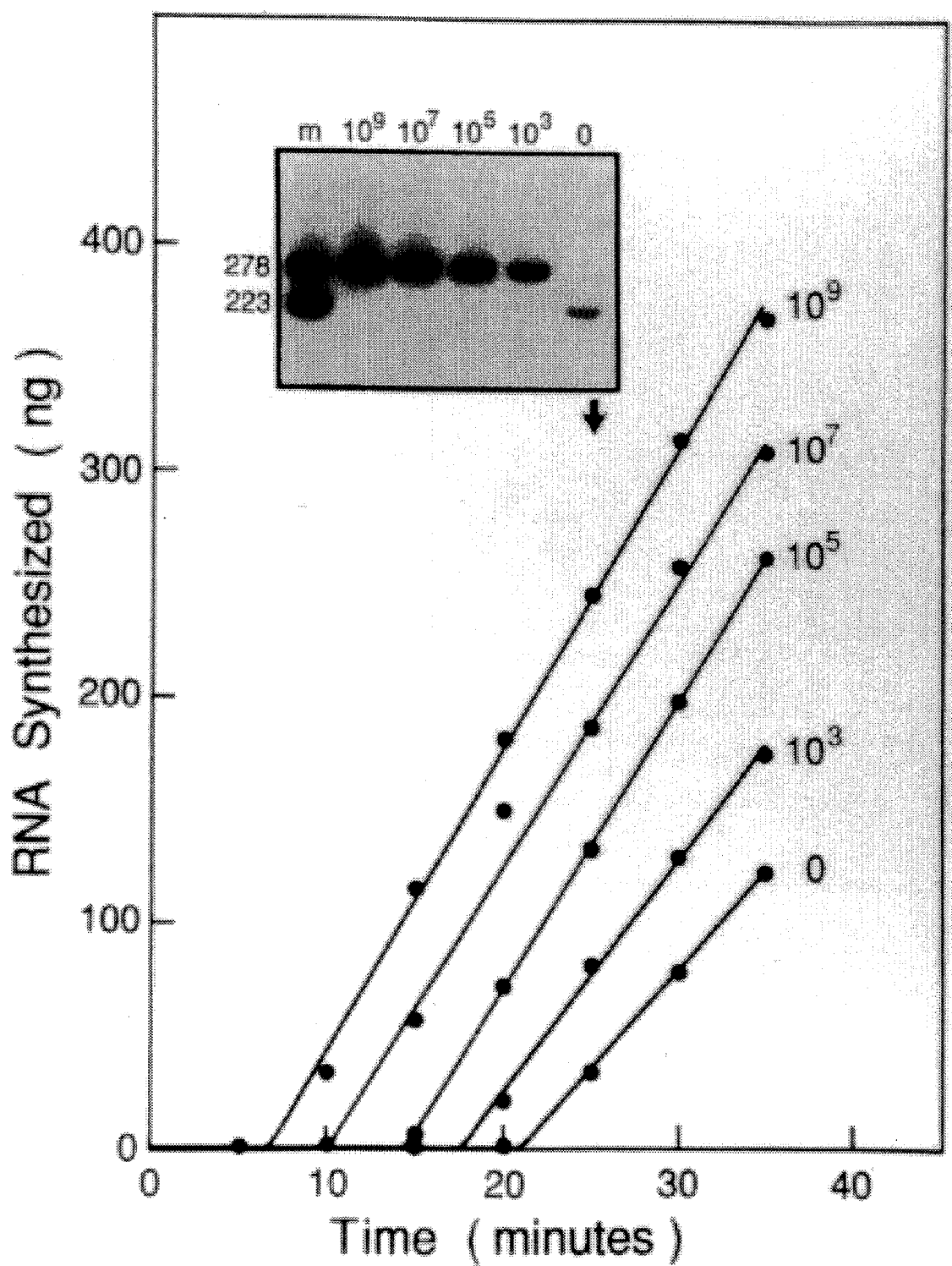
Figure 5:
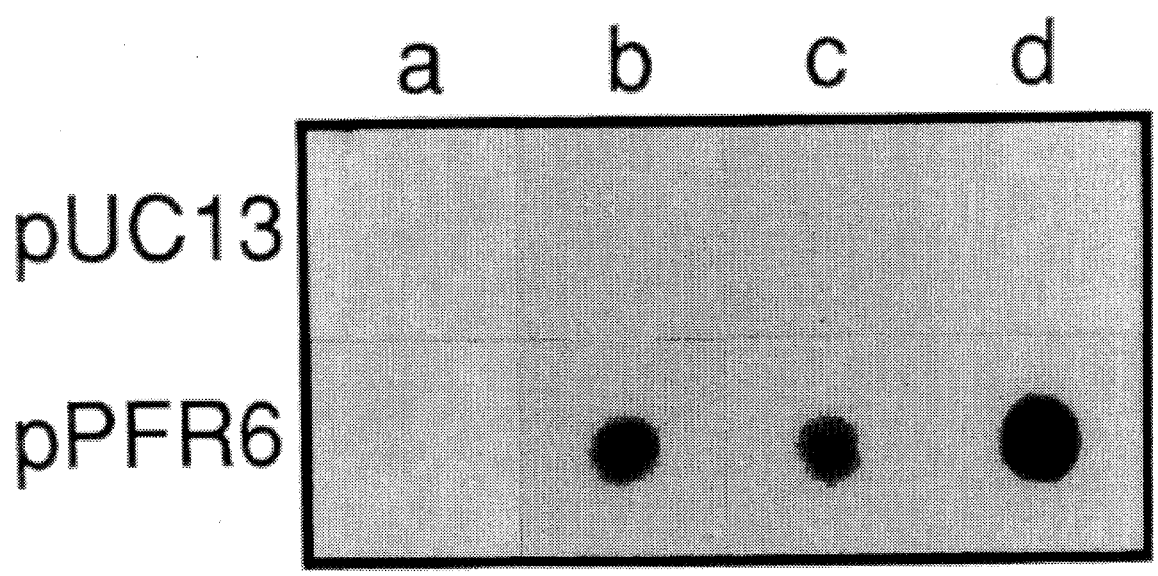
Figure 6:
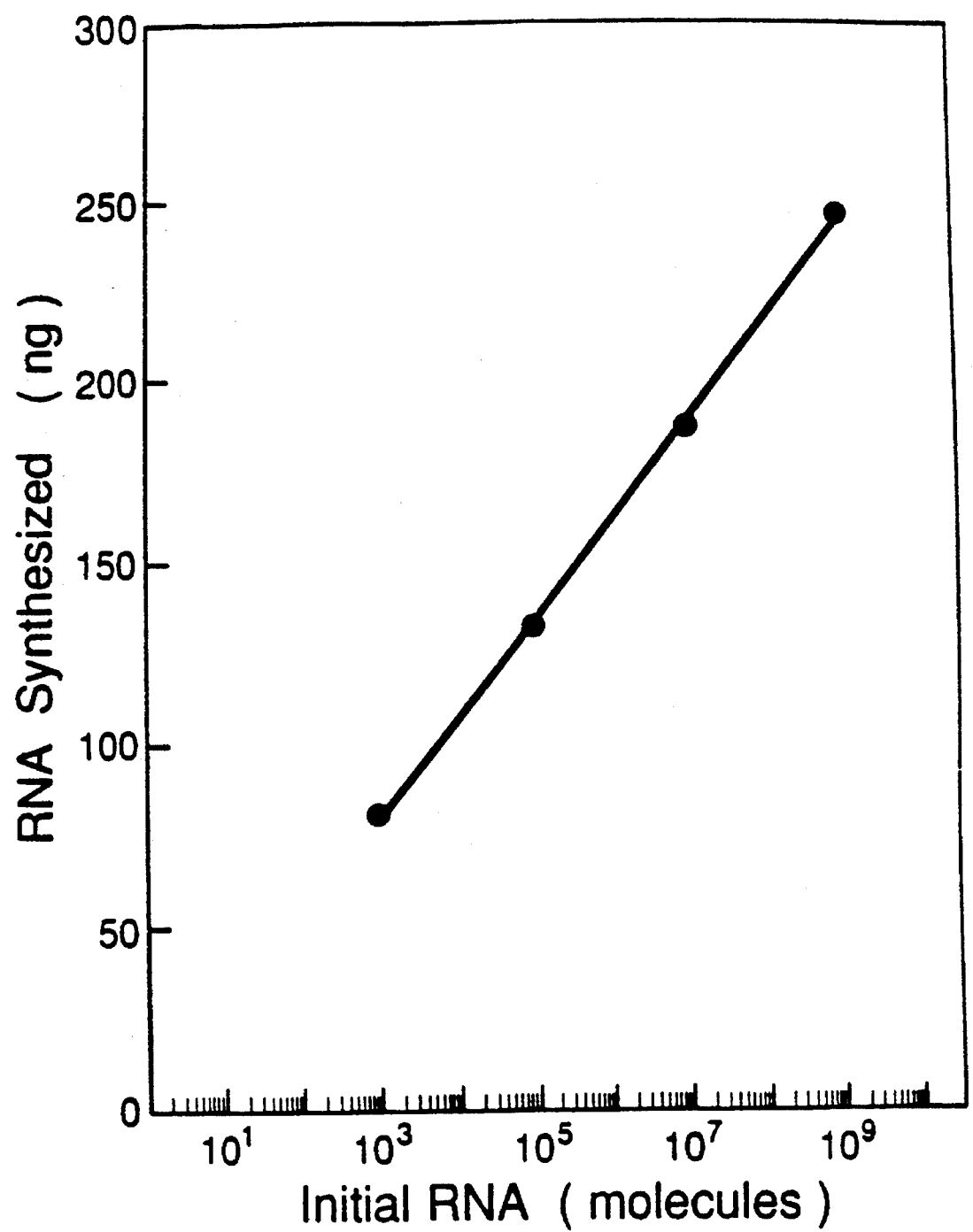

In most bioassays that employ molecular probes, the amount of probe bound is proportional to the number of targets. Amplification schemes, such as those employing enzymatic reporter groups (Leary, et al. 1983) or polymerase chain reactions (Saiki, et al. 1985; Saiki, et al. 1988; Erlich, et al. 1988), enable a small number of targets to be detected. However, the relationship between the size of the amplified signal and the number of targets is still linear. The unique kinetic characteristics of Qβ replicase reactions should permit the design of bioassays in which the size of the amplified signal is linearly proportional to the logarithm of the number of targets. FIG. 6 utilizes data from the experiment shown in FIG. 4 to illustrate this relationship: the logarithm of the number of recombinant RNA molecules initially present in each reaction was plotted against the amount of RNA synthesized in 25 minutes (by which time each reaction had completed the exponential phase of synthesis). The amount of recombinant RNA initially added to those reactions can be thought of as representing the amount of probe that would have been bound to targets had this been an actual assay, and the amount of amplified RNA at 25 minutes simulates the signal that would have been detected. The results show that the size of the amplified signal would be in the hundred-nanogram range whether the number of targets was as small as one thousand or as large as one billion. Thus, bioassays employing amplification by Qβ replicase should be able to detect targets over a range of at least six orders of magnitude.

Theoretically, assays employing Qβ replicase should be extremely sensitive, because such reactions can be initiated with as little as one molecule of template RNA (Levisohn and Spiegelman, 1968). In practice, the sensitivity of assays will be limited by the level of persistence of nonspecifically bound probes. In the experiments described above it was found that 600,000 molecules of MDV-fal-un RNA had bound nonspecifically to nitrocellulose dot-blots that contained 1.5 μg of pUC13 DNA. It is apparent that a different hybridization technique will be required to test the limits of sensitivity of assays employing replicatable probes. There are a number of promising methods that should result in a markedly reduced background, including those where hybridization occurs in solution (Kohn, et al. 1977; Pellegrino, et al. 1987; Urdea, et al. 1987) and those that employ "sandwich" hybridization techniques (Palva and Ranki, 1985). By combining an effective background reduction technique with the enormous amplification inherent in the use of replicatable probes, it should be possible to develop assays that can detect a few hundred molecules of target. This would permit the detection of relatively rare RNA or DNA molecules in a research sample and the detection of even a single infectious agent in a clinical sample.

Replicatable recombinant RNAs containing a variety of inserted sequences have recently been constructed. This leads one to believe that, by choosing appropriate inserts, recombinant RNA probes can be prepared that will be able to detect the nucleic acid of any virus, bacterium, or eukaryotic parasite.

Amplified recombinant RNAs contain a sequence (the probe) that identifies which target was detected. It should therefore be possible to design diagnostic assays that utilize a mixture of recombinant RNAs, each containing a probe sequence specific for the genome of a different infectious agent. After amplification with Qβ replicase, the RNA population would contain replicates of only those probes that had bound to their targets. Subsequent hybridization of these amplified RNAs to a membrane containing an ordered array of DNA dot-blots complementary to each of the probes would permit the simultaneous identification of several different organisms in the same sample.

EXAMPLE 2

We prepared a recombinant RNA that contained a 30-nucleotide-long probe complementary to a conserved region of the pol gene in human immunodeficiency virus type 1 (HIV-1) mRNA. Test samples were prepared, each containing a different number of HIV-1 transcripts that served as simulated HIV-1 mRNA targets. Hybridizations were carried out in a solution containing the chaotropic salt, guanidine thiocyanate. Probe-target hybrids were isolated by reversible target capture on paramagnetic particles. The probes were then released from their targets and amplified by incubation with the RNA-directed RNA polymerase, Qβ replicase. The replicase copied the probes in an exponential manner: after each round of copying, the number of RNA molecules doubled. The amount of RNA synthesized in each reaction (approximately 50 ng) was sufficient to measure without using radioisotopes. Kinetic analysis of the reactions demonstrated that the number of HIV-1 targets originally present in each sample could be determined by measuring the time it took to synthesize a particular amount of RNA (the longer the synthesis took, the fewer the number of targets originally present). The results suggest that clinical assays involving replicatable hybridization probes will be simple, accurate, sensitive, and automatable.

Materials and Methods

Enzymes and Oligodeoxyribonucleotides

Bacteriophage T7 RNA polymerase (EC 2.7.7.6) was purchased from New England Biolabs, Beverly, Mass., and calf thymus terminal deoxyribonucleotidyltranferase (EC 2.7.7.31) was obtained from Supertechs, Bethesda, Md. Qβ replicase (EC 2.7.7.48) was isolated from bacteriophage Qβ-infected *Escherichia coli* Q13 by the procedure of Eoyang and August (Eoyang and August, 1971), with the hydroxylapatite step omitted. Qβ replicase is stable when stored in a glycerol solution at −20° C.: its activity remains unchanged after five years of storage. Single-stranded DNA fragments were prepared, using β-cyanoethyl phosphoramidite chemistry, on an Applied Biosystems 380A synthesizer, Foster City, Calif.

Replicatable HIV-I Probes

Figure 7:
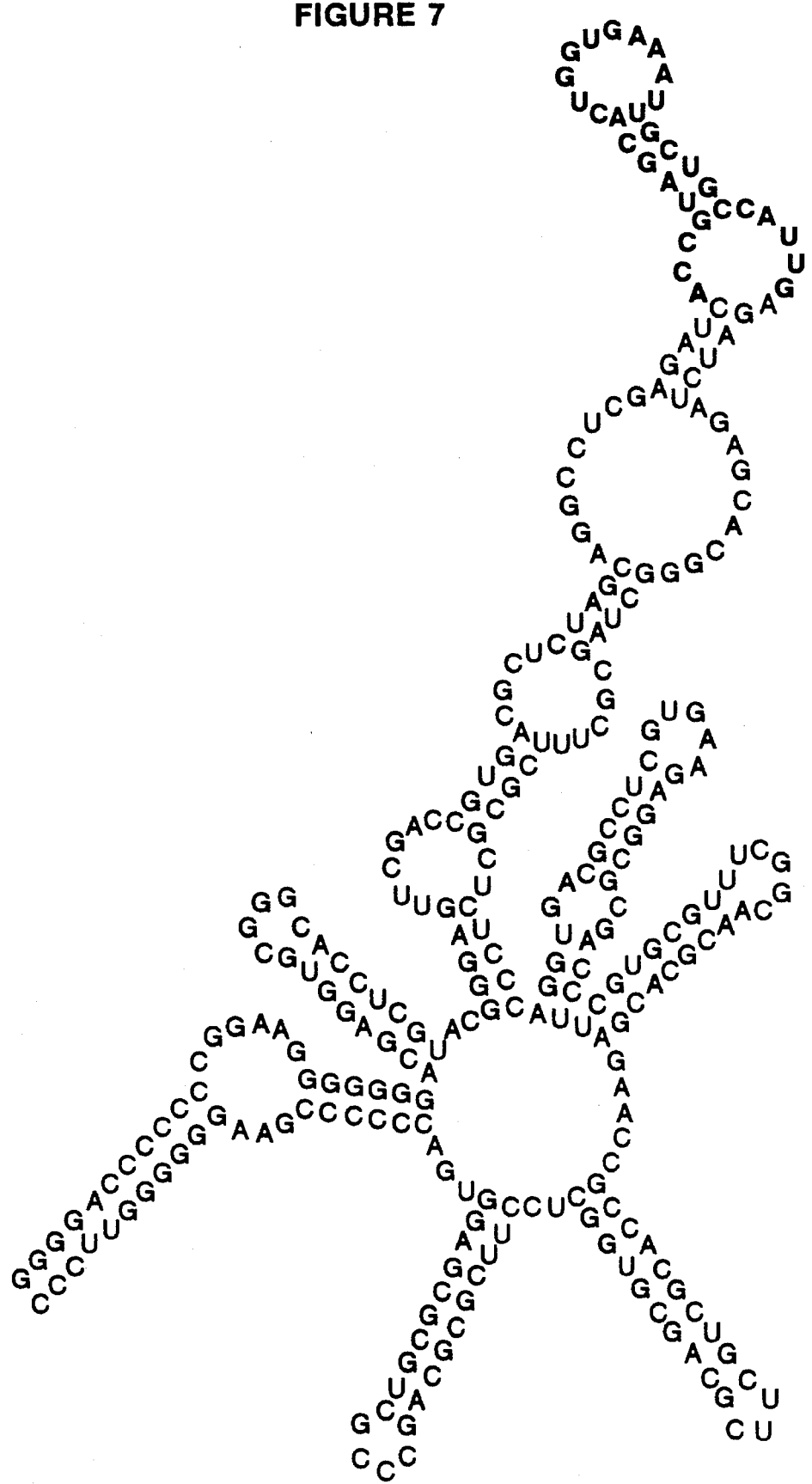

Recombinant MDV-1 RNA containing an inserted HIV-1 probe sequence was synthesized by transcription from a recombinant plasmid. The plasmid was constructed by inserting a synthetic probe sequence (prepared by annealing dGATCACCGTAGCACTGGTGAAATTGCTGCCATTGA to dGATCTCAATGGCAGCAATTTCACCAGT-GCTACGGT) into the Bgl II site of a plasmid that is identical to plasmid pT7-MDV-poly (Lizardi, et al. 1988), except that the polylinker sequence is in the opposite orientation. The nucleotide sequence in the recombinant region of the cloned plasmid was confirmed by the chain termination procedure (Sanger, et al. 1977). The synthesis of replicatable probes by transcription from linearized recombinant plasmids with T7 RNA polymerase is described in detail elsewhere (Lizardi, et al. 1988). The resulting transcripts were recombinant MDV-1(+) RNAs containing a 30-nucleotide-long probe sequence that is complementary to nucleotides 4622–4651 in the pol gene of HIV-1 genomic RNA (Meusing, et al. 1985). FIG. 7 shows the nucleotide sequence and predicted secondary structure of the transcribed RNA. MDV-hiv (+) RNA serves as an excellent template for exponential amplification by Qβ replicase.

Capture Probes

Single-stranded DNAs containing 3'-poly(dA) tails were synthesized for use in binding probe-target hybrids to oligo(dT) groups on the surface of paramagnetic particles. Four different oligodeoxyribonucleotides (of lengths 24, 40, 40, and 43 nucleotides) were prepared by automated synthesis. Each probe was complementary to a different region of the HIV-1 pol gene near to the target of the replicatable probe. A poly(dA) tail was added to the 3' end of each probe by incubation with terminal deoxyribonucleotidyltransferase (Nelson and Brutlag, 1979).

Hybridization

Simulated HIV-1 mRNA targets were purchased from Gene-Trak Systems, Framingham, Mass. These transcripts included a complete copy of the HIV-1 pol gene. Seven reaction tubes were prepared. Each contained simulated HIV-1 mRNA targets, MDV-hiv (+) RNA (replicatable probes), and capture probes, dissolved in 70 μL of 2.5 mol/L guanidine thiocyanate (Fluka Chemical, Hauppage, N.Y.), and placed in a polypropylene "titertube" (Bio-Rad, Richmond, Calif.). Each tube contained $2 \times 10^9$ molecules of MDV-hiv (+) RNA, $10^{11}$ molecules of each capture probe, and a different number of target molecules. The number of HIV-1 transcripts in each tube was: $10^9$, $10^8$, $10^7$, $10^6$, $10^5$, $10^4$, and $10^3$. The tubes were incubated at 37° C. for 18 h.

Reversible Target Capture

Figure 8:
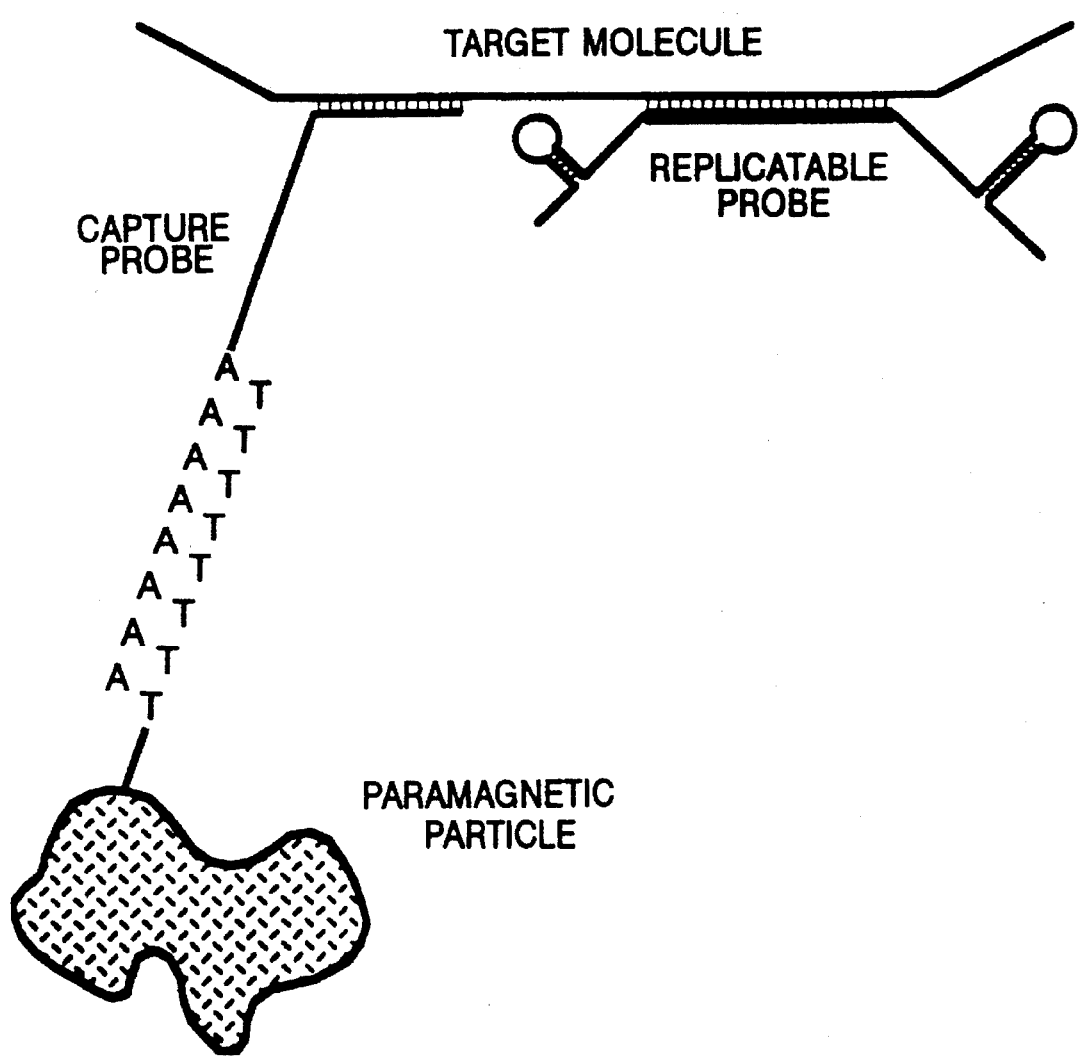

After the completion of hybridization, the probe-target hybrids were isolated from the reaction mixture by binding them to oligo(dT) groups on the surface of paramagnetic particles (Morrisey, et al. 1989). These ferric oxide particles (<1 μm in diameter), purchased from Gene-Trak Systems, possess highly convoluted surfaces coated with silicon hydrides to which numerous oligo(dT) "hairs" have been covalently linked. We added 50 μL of a suspension of paramagnetic particles to each reaction tube, reducing the guanidine thiocyanate (GuSCN) concentration to 1.45 mol/L. The tubes were incubated at 37° C. for 10 min to allow the 3'-poly(dA) tails of the capture probes to hybridize to the oligo(dT) groups on the surface of the particles. The number of oligo(dT) groups available on the surface of the particles far exceeded the number of capture probes present in the reaction. Because the target molecules are hybridized to the 5' end of the capture probes, the probe-target hybrids become linked to the surface of the particles (FIG. 8). If these had been actual clinical assays, and polyadenylated mRNAs had been present in the samples, the mRNAs would not have bound to the particles, because the poly(rA) on the end of an mRNA forms a much weaker bond with oligo(dT) in concentrated GuSCN solutions than does the poly(dA) on the end of a capture probe (Morrissey, et al. 1989).

Because the particles are paramagnetic, they do not act as magnets, and they do not cling to each other. However, when placed in a magnetic field, they are drawn to the magnetic source. Accordingly, the paramagnetic particles, with the probe-target hybrids bound to their surface, were drawn to the walls of the titertubes by placing the tubes in the presence of the strong magnetic field provided by a magnetic separation device (which was purchased from Gene-Trak Systems). The supernates, which contained the nonhybridized probes, were then withdrawn from each tube by aspiration, and replaced by 200 μL of a wash solution containing GuSCN at 1.5 mol/L. The tubes were then withdrawn from the magnetic field and the probe-target hybrids attached to the resuspended particles were washed by vigorous agitation on a multi-tube vortex-type mixer (American Hospital Supply, McGaw Park, Ill.). The particles were again drawn to the walls of the tubes, the supernates were aspirated, another 200 μL of 1.5 mol/L GuSCN wash solution was added, and the particles were again agitated and drawn to the walls of the tubes. The supernates were again withdrawn by aspiration, but this time they were replaced with 50 μL of a release solution containing GuSCN at 3.25 mol/L.

The tubes were again removed from the magnetic field, agitated to resuspend the particles, and then incubated at 37° C. for 5 min. In this more concentrated GuSCN solution, the relatively weak hybrids formed between the 3'-poly(dA) tails of the capture probes and the oligo(dT) groups on the surface of the particles came apart, releasing the probe-target hybrids back into solution. However, the much stronger hybrids formed between the capture probes and the target (and between the replicatable probe and the target) remained intact (Morrissey, et al. 1989). The stripped particles were then drawn to the sides of the tubes, and the supernates (containing the released probe-target hybrids) were transferred to new tubes. The stripped particles were discarded and 50 µL of a suspension of fresh particles was added to each new tube, reducing the GuSCN concentration to 1.62 mol/L. The tubes were incubated at 37° C. for 10 min to allow the probe-target hybrids to be recaptured by the hybridization of the 3'-poly(dA) tails of the capture probes to the oligo(dT) groups on the surface of the new particles.

Transferring the probe-target hybrids from one set of solid surfaces to a new set of solid surfaces effectively removed any nonhybridized probes that adhere to surfaces. The entire washing process was repeated three times, which markedly reduced the number of nonhybridized probes (Morrissey, et al. 1989). After the probe-target hybrids were captured onto the surface of particles for the third time, we washed them once in 200 µL of 1.5 mol/L GuSCN, and then twice in 200 µL of a solution containing 100 mmol/L KCl (a nonchaotropic salt that preserves the hybrids) to wash away the GuSCN. After removing the supernate from the last 100 mmol/L KCl wash by aspiration, we resuspended the particles in 50 µL of 10 mmol/L Tris-HCl buffer (pH 8.0) containing 1 mmol of EDTA per liter. The resuspended particles were then incubated in this salt-free buffer at 37° C. for 10 min, which completely dissociated the probe-target hybrids. The particles were then drawn to the walls of the tubes, leaving in each tube a supernate that contained an amount of MDV-hiv (+) RNA proportional to the number of target molecules originally present.

Exponential Amplification

We prepared seven replication reactions (Kramer, et al. 1974), each containing 35 µL of the final supernate from the corresponding hybridization reaction. These MDV-hiv (+) RNA molecules were then amplified by incubation with 5.76 µg of Qβ replicase at 37° C. in 105 µL of a solution containing, per liter, 400 µmol of ATP, 40 µmol of [$\alpha$-$^{32}$P] CTP, 400 µmol of UTP, 7.5 mmol of $MgCl_2$, and 45 mmol of Tris-HCl (pH 7.5). The reactions were incubated in parallel, and 4-µL aliquots were withdrawn from each of the seven reactions at one-min intervals between 9 and 29 min of incubation and mixed with 36 µL of an ice-cold solution containing 120 µmol of NaCl and 20 mmol of EDTA-NaOH (pH 8) per liter. The EDTA in this solution chelated the magnesium in the sample, preventing further replication.

The size and homogeneity of the [$^{32}$P]RNA products in 5-µL aliquots of each of the 147 samples was determined by electrophoresis through 8% polyacrylamide slab gels in the presence of urea, 7 mol/L (Maniatis and van desande, 1975). Finally, the [$^{32}$P]RNA products in a 10-µL aliquot of each of the 147 samples were precipitated by the addition of 190 µL of an ice-cold solution containing 360 mmol of phosphoric acid, 20 mmol of sodium pyrophosphate, and 2 mmol of EDTA per liter. The precipitated RNA in each sample was then electrostatically bound to a "Zeta-Probe" quaternary-amine-derivatized nylon membrane(Bio-Rad) in a dot-blot vacuum filtering manifold (Bio-Rad). Each bound sample was washed 10 times with 200 µL of the ice-cold precipitation solution to remove unincorporated [$^{32}$P]CTP. The membrane was then air-dried, and the amount of [$^{32}$P]RNA present in each sample on the membrane was made visible by autoradiography. After the autoradiograph was prepared, the amount of RNA present in each dot-blot was measured in a scintillation counter.

Results

We carried out assays in which replicatable HIV-1 probes were hybridized to serial dilutions of simulated HIV-1 mRNA target molecules in the presence of guanidine thiocyanate (Thompson and Gillespie, 1987). After hybridization, the resulting probe-target hybrids were isolated by three cycles of reversible target capture (Morrissey, et al. 1989) on paramagnetic particles. The hybridized probes were then released from their targets and exponentially amplified by incubation with Qβ replicase (Lizardi, et al. 1988), with samples of each reaction being taken at one-minute intervals. Electrophoretic analysis of the size and homogeneity of the RNA in each sample indicated that only MDV-hiv RNA was synthesized.

An aliquot of each sample was bound to a nylon membrane in a dot-blot filtration apparatus, and the [$^{32}$P]MDV-hiv RNA in each aliquot was made visible by autoradiography. In the resulting autoradiogram (FIG. 9), the density of each spot indicates the amount of RNA present at each time point. After preparing each autoradiogram, the amount of RNA in each sample was measured with a scintillation counter. The results showed that although no RNA is apparent in the early time points, this is the period in which the RNA population increased exponentially (Haruna and Spiegelman, 1965a). The RNA became visible in the autoradiogram at about the same time that the number of RNA molecules equaled the number of active replicase molecules (the "saturation point"). From that time on, the RNA population increased linearly (Kramer, et al. 1974). Thus, at those times when the RNA is visible in each reaction, the RNA population is increasing linearly.

The results demonstrate that the time at which the saturation point occurs in each amplification reaction is a function of the number of target molecules originally present in the corresponding hybridization reaction. The fewer target molecules that were originally present, the fewer the replicatable probes that were bound to targets, and thus, the fewer replicatable probes that were available to initiate the amplification reaction. Because amplification reactions initiated with fewer replicatable probes must undergo more doublings of the RNA population before there are enough RNA molecules to achieve saturation, the kinetic data can be used to calculate the number of replicatable probes that were present at the beginning of the reaction. If known standards are included among the unknown samples be tested, then these data can be used to determine the number of target molecules originally present in each unknown sample.

The results also indicate the limit of detection. The amplification reaction corresponding to the sample containing $10^5$ targets achieved saturation at an earlier time than did the amplification reaction corresponding to the sample containing $10^4$ targets. However, there was no significant difference in the amplification reactions corresponding to the samples containing $10^4$ and $10^3$ targets. However, there was no significant difference in the amplification reactions corresponding to the samples containing $10^4$ and $10^3$ targets. These results indicate that the limit of detection was about 10,000 target molecules. Because electrophoretic analysis of the amplified RNA in each sample indicated that only recombinant RNA was synthesized, the limit of detection was determined by the level of persistence of nonhybridized replicatable probes. We feel that it is important to note that these were only preliminary assays, designed to demonstrate how replicatable probes might be used. Further experiments should lead to alterations in the assay format that will improve the sensitivity.

The assay we have described demonstrates that replicatable hybridization probes can be used in quantitative assays designed to detect rare targets. It is clear that these assays are simple, accurate, sensitive, and automatable.

EXAMPLE 3

To enable the simultaneous determination of the levels of HTLV-I, HTLV-II, HIV-1, and HIV-2 in a single blood sample, all four recombinant-RNA probes are added to the same assay tube. After amplification, the resulting mixture of recombinant RNA products is sorted into separate species by hybridizing to an ordered array of dot-blots, each of which contains DNA complementary to one of the probe sequences.

Species-specific hybrization probes for the detection of HTLV-I, HTLV-II, HIV-1, and HIV-2 are derived from a highly conserved region of the viral pol gene, and form a specific hybrid with the corresponding retroviral mRNA. They are each 40 nucleotides long. The selected probe sequences are listed in Table 2. The identification of the target region is based on the following sequence determinations: HTLV-I (Seiki et al., 1983), HTLV-II (Shimotohno et al., 1985), HIV-1 (Ratner et al., 1985; Muesing et al., 1985), and HIV-2 (Guyader et al., 1987).

spread of pathogenic retroviruses precludes the fractionation of cells or the isolation of subcellular components and necessitates the use of solution hybridization. Also, it is necessary to employ an extremely efficient means of removing the unhybridized probes because unhybridized probes are amplified by Qβ replicase along with the hybridized probes. Hybridization is extremely efficient in solutions of the chaotropic agent, guanidine thiocyanate (Thompson and Gillespie, 1987). Concentrated solutions of guandine thiocyanate lyse cells, denature all proteins (including nucleases), liberate nucleic acids from cellular matrices, and unwind DNA molecules, permitting hybridization to occur without interference from cellular debris (Pellegrino et al., 1987). The "reversible target capture" procedure (Morrissey et al., 1989) is an improved "sandwich hybridization" tech-

TABLE 2

Probe Sequences for Detecting Human Retroviruses

| Virus | Sequence in Recombinant RNA | Target Region |
| --- | --- | --- |
| HTLV-I | 5'-GUCUAUAGUUUGCAAGUGGGCUAGUGUGGUUGGCAGGCUG-3' | 2821–2860 |
| HTLV-II | 5'-UAAGGGAGUCUGUGUAUUCAUUGAAGGUGGAAAUUGGGUC-3' | 4237–4376 |
| HIV-1 | 5'-GGCUUCUCCUUUUAGCUGACAUUUACUCACAGCUGGCUACU-3' | 4382–4421 |
| HIV-2 | 5'-UACUAUUGUUUCUAUUGUAUUUGCCUGUUCUCUGAUUCUA-3' | 4546–4585 |

The recombinant-RNA probes are prepared by transcription from corresponding recombinant plasmids (Lizardi et al., 1988). Synthetic oligodeoxyribonucleotides containing the probe sequence and appropriate sticky ends cloned into the polylinker region of pT7-MDV-poly are isolated and characterized by restriction mapping and confirmed by nucleotide sequence analysis (Wallace et al., 1981). Transcripts are prepared by incubating Sma I-cleaved plasmids with T7 RNA polymerase, and their sequences confirmed by the chain-termination procedure (Sanger et al., 1977) utilizing reverse transcriptase and a primer that initiates synthesis upstream from the region containing the probe sequence (Lane et al., 1985). The transcripts are incubated with Qβ replicase, and the resulting product RNAs analyzed by polyacrylamide gel electrophoresis to confirm their identity and homogeneity. The kinetics of synthesis of Qβ replicase reactions initiated with different concentrations of each recombinant-RNA probe is compared to MDV-1 RNA controls. And finally, the ability of each probe to hybridize well is confirmed with filter hybridization assays (Kafatos et al., 1979) employing model targets prepared by inserting appropriate retroviral targets into pUC19 DNA. The recombinant-RNA probes are used in clinical assays designed to detect retroviral sequences after being fully tested as described supra.

For the simultaneous determination of the levels of HTLV-I, HTLV-II, HIV-1, and HIV-2 in a single blood sample, all four recombinant-RNA probes are added to the same tube. After hybridization and amplification, the product RNA consists of a mixture of the different recombinant RNAs, whose relative abundance reflects the concentration of the different retroviral targets in the sample. This mixture of amplified probes is hybridized to a dipstick containing an ordered array of dot-blots (Kafatos et al., 1979), each of which contains DNA complementary to one of the probe sequences. In this manner, the different recombinant RNAs are sorted out, allowing the amount of each retroviral species to be measured.

EXAMPLE 4

A fast and simple format permitting the testing of the large number of blood samples that must be tested to control the nique (Ranki et al., 1983; Syvanen et al., 1986), in which probe-target hybrids are bound to the surface of magnetic beads. After washing to remove unhybridized probes, the hybrids are released from the beads, and then bound to a new set of beads for another round of washing. By repeating this procedure several times, the concentration of unhybridized probes is reduced at least seven orders of magnitude (Morrissey et al., 1989). Therefore, the use of guanidine thiocyanate in combination with reversible target capture provides a blood sample assay format in which cells do not have to be lysed before the assay is performed, and unhybridized probe is removed before amplification.

By transferring the target-probe hybrids from one solid surface to another, non-specifically bound probes that adhere to solid surfaces are effectively removed. This entire washing process is repeated three times, resulting in a dramatic reduction in the amount of unhybridized probe (Morrissey, et al, 1989). In the final cycle, the GTC is washed away from the beads and replaced with a salt-free buffer, and the mixture incubated at 37° C. to free the recombinant-RNA reporter probes from their targets. The magnetic beads are then removed, leaving behind a solution containing an amount of recombinant RNA that is proportional to the number of target sequences that were present in the original sample. Finally, an aliquot of this solution is incubated for 30 minutes at 37° C. in a 50-µL reaction containing 5 µg Qβ replicase to exponentially amplify the freed recombinant-RNA probes.

The amount of RNA that is synthesized in these assays is determined by the incorporation of radioactive precursors. In a clinical setting, in which the assays would be automated, it is preferable to detect the synthesized RNA by the fluorescence that occurs when ethidium bromide binds to RNA. Since these assays are incubated long enough for the replicase to become saturated with RNA, the amount of RNA synthesized by the end of the incubation period is directly proportional to the logarithm of the number of target sequences that were present in the original sample (Lizardi, et al., 1988). The inclusion of samples containing known standards, along with the unknown samples to be assayed, permits the direct determination of the number of molecular targets that were present in each sample.

REFERENCES

Abbott, M. A., Poiesz, B. J., Byrne, B. C., Kwok, S., Sninsky, J. J., and Ehrlich, G. D. (1988) J. Infect. Dis. 158, 1158–1169. Enzymatic Gene Amplification: Qualitative and Quantitative Methods of Detecting Proviral DNA Amplified in Vitro.

Aslund, L., Franzen, L., Westin, G., Persson, T., Wigzell, H. and Pettersson, U. (1985) J. Mol. Biol. 185, 509–516.

Axelrod, V. D., and Kramer, F. R. (1985) Biochemistry 24, 5716–5723. Transcription from Bacteriophage T7 and SP6 RNA Polymerase Promoters in the Presence of 3'-Deoxyribonucleoside 5'-Triphosphate Chain Terminators.

Bausch, J. N., Kramer, F. R., Miele, E. A., Dobkin, C., and Mills, D. R. (1983) J. Biol. Chem. 258, 1978–1984. Terminal Adenylation in the Synthesis of RNA by Qβ Replicase.

Bailey, J. M. and Davidson, N. (1976) Anal. Biochem. 70, 75–85.

Biebricher, C. K., Kiekmann, S., and Luce, R. (1982) J. Mol. Biol. 154, 629–648. Structural Analysis of Self-replicating RNA Sythesized by Q-beta Replicase.

Biggin, M. D., Gibson, T. J. and Hong, G. F. (1983) Proc. Natl. Acad. Sci. USA 80, 3963–3965.

Bywater, M., Bywater, R. and Hellman, L. (1983) Anal. Biochem. 132, 219–224.

Chamberlin, M., and Ring, J. (1973) J. Biol. Chem. 248, 2235–2244. Characterization of T7-specific Ribonucleic Acid Polymerase. 1. General Properties of the Enzymatic Reaction and the Template Specificity of the Enzyme.

Chu, B. C. F., Kramer, F. R. and Orgel, L. E. (1986) Nucleic Acid Res. 14, 5591–5603. Synthesis of an Amplifiable Reporter RNA for Bioassays.

Clavel, F., Guetard, D., Brun-Vezinet, F., Chamaret, S., Rey, M. A., Santos-Ferreira, M. O.,Laurent, A. G., Dauguet, C., Katlama, C., Rouzioux, C., Klatzmann, D., Champalimaud, J. L., nd Montagnier, L. (1986) Science 233, 343–346. Isolation of a New Human Retrovirus from West African Patients with AIDS.

Cosstick, R., McLaughlin, L. W. and Eckstein, F. (1984) Nucleic Acids Res. 12, 1791–1810.

Curran, J. W., Morgan, W. M., Hardy, A. M., Jaffe, H. W., Darrow, W. W., and Dowdle, W. R. (1985) Science 229, 1352–1357. The Epidemiology of AIDS: Current Status and Future Prospects.

Dahlberg, A. E., Dingman, C. W. and Peacock, A. C., (1969) J. Mol. Biol. 41, 139–147.

Dingman, C. W. and Peacock, A. C., (1968) Biochemistry 7, 2038–2044.

Dobkin, C., Mills, D. R., Kramer, F. R., and Spiegelman, S. (1979) Biochemistry 18, 2038–2044. RNA Replication: Required Intermediates and the Dissociation of Template, 67 Product, and Qβ Replicase.

Eoyang, L., and August, J. T. (1971) In: Procedures in Nucleici Acid Research, Vol. 2 (Cantoni, G. L., and Davis, D. R., eds.), pp. 829–839. Harper and Row, New York, N.Y. Qβ RNA Polymerase from Phage Qβ-infected E. coli.

Erlich, H. A., Gelfand, D. H. and Saiki, R. K. (1988) Nature 331, 461–462.

Fauci, A. S. (1986) Proc. Natl. Acad. Sci. USA 83, 9278–9283. Current Issues in Developing a Strategy for Dealing with the Acquired Immunodeficiency Syndrome.

Forster, A. C., Melnnes, J. L., Skingle, D.C., Symons, R. H. (1985), Nucleic Acids Res. 13(3), 745–761.

Franzen, L., Westin, G., Shabo, R., Aslund, L., Perlmann, H., Persson, T., Wigzell, H. and Pettersson, U. (1984) Lancet 1, 525–528.

Gait, M. J. (1984) Oligonucleotide Synthesis, IRL Press, Oxford.

Gillespie, D., and Spiegelman, S. (1965) J. Mol. Biol. 12, 829–842. A Quantitative Assay for DNA-RNA Hybrids with DNA Immobilized on a Membrane.

Guyader, M., Emerman, M., Sonigo, P., Clavel, F., Montagnier, L., and Alizon, M. (1987) Nature 326, 662–669. Genome Organization and Transactivation of the Human Immunodeficiency Virus Type 2.

Harper, M. E., Marselle, L. M., Gallo, R. C., and Wong-Staal, F. (1986) Proc. Natl. Acad. Sci. USA 83, 772–776. Detection of Lymphocyte Expression of Human T-lymphotropic Virus Type III in Lymph Nodes and Peripheral Blood from Infected Individuals by in situ Hybridization.

Haruna, I., and Spiegelman, S. (1965a) Proc. Natl. Acad. Sci. USA 54, 579–587. Specific Template Requirements of RNA Replicases.

Haruna, I., and Spiegelman, S. (1965b) Science 150, 884–886. Autocatalytic Synthesis of a Viral RNA in vitro.

Haruna, I., and Spiegelman, S. (1965c) Proc. Natl. Acad. Sci. USA 54, 1189–1193. Recognition of Size and Sequence by an RNA Replicase.

Haseloff, J., and Gerlach, W. L. (1988) Nature 334, 585–591. Simple RNA Enzymes with New and Highly Specific Endoribonuclease Activities.

Hill, D., and Blumenthal, T. (1983) Nature 301, 350–352. Does Qβ Replicase Synthesize RNA in the Absence of Template?

Holmes, D. S. and Quigley, M. (1981) Anal Biochem. 114, 193–197.

Igloi, G. L. (1983) Anal. Biochem. 134, 184–188.

Kacian, D. L., Mills, D. R., Kramer, F. R., and Spiegelman, S. (1972) Proc. Natl. Acad. Sci. USA 69, 3038–3042. A Replicating RNA Molecule Suitable for a Detailed Analysis of Extracellular Evolution and Replication.

Kafatos, F. C., Jones, C. W., and Efstratiadis, A. (1979) Nucleic Acids Res. 7, 1541–1552. Determination of Nucleic Acid Sequence Homologies and Relative Concentrations by a Dot Hybridization Procedure.

Kalyanaraman, V. S., Sarnagadharan, M. G., Robert-Gurodd, M., Miyoshi, I., Golde, D., and Gallo, R. C. (1982) Science 218, 571–573. A New Type of Human T-cell Leukemia Virus (HTLV-II) Associated with a T-cell Variant of Hairy Cell Leukemia.

Klotz, G., Kramer, F. R., and Lkeinschmidt, A. K. (1980) Electron Microscopy 2, 530–531. Conformational Details of Partially Base-paired Small RNAs in the Nanometer Range.

Kohne, D. E, Levison, S. A. and Byers, M. J. (1977) Biochemistry 16, 5329–5341.

Kramer, F. R., Mills, D. R., Cole, P. E., Nishihara, T., and Spiegelman, S. (1974) J. Mol. Biol. 89, 719–736. Evolution in vitro: Sequence and Phenotype of a Mutant RNA Resistant to Ethidium Bromide.

Kramer, F. R., and Mills, D. R. (1978) Proc. Natl. Acad. sci. USA 75, 5334–5338. RNA Sequencing with Radioactive Chain-terminating Ribonucleotides.

Kramer, F. R., and Mills, D. R. (1981) Nucleic Acids Res. 9, 5109–5124. Secondary Structure Formation during RNA Synthesis.

Kramer, F. R., Mills, D. R., and Rudner, R. (1989) J. Mol. Biol., in preparation. Selection of a Mutant RNA Resistant to Ribonuclease $T_1$.

Kutateladze, T. V., Axelrod, V. D., Gorbulve, V. G., Belzhelarskaya, S. N. and Vartikyan, R. M. (1979) Anal. Biochem. 100, 129–135.

LaFlamme, S. E., Kramer, F. R., and Mills, D. R. (1985) Nucleic Acids Res. 13, 8425–8440. Comparison of Pausing during Transcription and Replication.

Lane, D. J., Pace, B., Olsen, G. J., Stahl, D. A., Sogin, M. L., and Pace, N. R. (1985) Proc. Natl. Acad. Sci. USA 82, 6955–6959. Rapid Determination of 16S Ribosomal RNA Sequences for Phylogenic Analyses.

Langer P. R., Waldrop A. A., Ward D.C. (1981) Enzymatic Synthesis of Biotin-labeled Polynucleotides: Novel Nucleic Acid Affinity Probes. Proc. Natl. Acad. Sci. USA 78:6633–7.

Leary, J. J., Brigati, and Ward, D.C. (1983) Proc. Natl. Acad. Sci. USA 80, 4045–4049. Rapid and Sensitive Colorimetric Method for Visualizing Biotin-labeled DNA Probes Hybridized to DNA or RNA Immobilized on Nitrocellulose: Bio-blots.

Levisohn, R., and Spiegelman, S. (1968) Proc. Natl. Acad. Sci. USA 60, 866–872. The Cloning of a Self-replicating RNA Molecule.

Lizardi P. M., Guerra C. E., Lomeli H., Tussie-Luna I., Kramer F. R. (1988) Exponential amplification of recombinant-RNA hybridization probes. Biotechnology 6:1197–202.

Lo, K. M., Jones, S. S., Hackett, N. R. and Khorana, H. G. (1984) Proc. Natl. Acad. Sci. USA 81 2285–2289.

Maniatis, T., Jeffrey, A. and van desande, H. (1975) Biochemistry 14, 3787–3794.

Matthes, H. W. D., Zenke, W. M. Grundstroem, T., Staub, A., Wintzerith, M. and Chambon, P. (1984) EMBO J. 3, 801–805.

Matthews, J. A., Batki, A., Hynds, C. and Kricka, L. J. (1985) Anal. Biochem. 151, 205–209.

Maxwell, I. H., Van Ness, J. and Hahn, W. E. (1978) Nucleic Acids Res. 5, 2033–2038.

McAllister, W. T., Morris, C., Rosenberg, A. H., and Studier, F. W. (1981) J. Mol. Biol. 153, 527–544. Utilization of Bacteriophage T7 Late Promoters in Recombinant Plasmids during Invention.

Melton, D. A., Krieg, P. A., Rabagliati, M. R., Maniatis, T., Zinn, K., and Green, M. R. (1984) Nucleic Acids Res. 12, 7035–7056. Efficient in vitro Synthesis of Biologically Active RNA and RNA Hybridization Probes from Plasmids containing a Bacteriophage SP6 promoter.

Miele, E. A., Mills, D. R., and Kramer, F. R. (1983) J. Mol. Biol. 171, 281–295. Autocatalytic Replication of a Recombinant RNA.

Mills, D. R., Axelrod, V. D., Tussle-Luna, I., Lizardi, P. M. and Kramer, F. R. (1988) manuscript in preparation.

Mills, D. R., Peterson, R. L., and Spiegelman, S. (1967) Proc. Natl. Acad. Sci. USA 58, 217–224. An Extracellular Darwinian Experiment with a Self-duplicating Nucleic Acid Molecule.

Mills, D. R., Kramer, F. R., and Spiegelman, S. (1973) Science 180, 916–927. Complete Nucleotide Sequence of a Replicating RNA Molecule.

Mills, D. R., Kramer, F. R., Kobkin, C., Nishihara, T., and Spiegelman, S. (1975) Proc. Natl. Acad. Sci. USA 72, 4252–4256. Nucleotide Sequence of Microvariant RNA: Another Small Replicating Molecule.

Mills D. R., Dobkin, C., and Kramer, F. R. (1978) Cell 15, 541–550. Template-determined, Variable Rate of RNA Chain Elongation.

Mills, D. R., and Kramer, F. R. (1979) Proc. Natl. Acad. Sci. USA 76, 2232–2235. Structure-independent Nucleotide Sequence Analysis.

Mills, D. R., Kramer, F. R., Dobkin, C., Nishihara, T., and Cole, P. E. (1980) Biochemistry 19, 228–236. Modification of Cytidines in a Qβ Replicase Template: Analysis of Conformation and Localization of Lethal Nucleotide Substitutions.

Mills, D. R., Axelrod, V. D., Tussie-Luna, I., Lizardi, P. M., and Kramer, F. R. (1990) Gene, in preparation. Exponential Replication of Recombinant RNAs Transcribed from Plasmids.

Mizusawa, S., Nishimura, S. and Seela, F. (1986) Nucleic Acids Res. 14, 1319–1324.

Morrissey, D. V., Lombardo, M., Eldredge, J. K., Kearney, K. R., Grody, E. P., and Collins, M. L. (1989) Anal. Biochem. in press. Nucleic Acid Hybridization Assays Employing Datailed Capture Probes. I. Multiple Capture Methods.

Muesing, M. A., Smith, D. H., Cabradilla, C. D., Benton, C. V., Lasky, L. A., And Capon, J. J. (1985) Nature 313, 450–458. Nucleic Acid Structure and Expression of the Human AIDS/Lymphadenopathy Retrovirus.

Mullis, K. B., and Faloona, F. A. (1987) Meth. Enz. 155, 335–350. Specific Synthesis of DNA in vitro via a Polymerase-catalyzed Chain Reaction.

Munishkin, A. V., Voronin, L. A., and Chetverin, A. B. (1988) Nature 333, 473–475. An in vivo Recombinant RNA Capable of Autocatalytic Synthesis by Qβ Replicase.

Nelson T, Brutlag D. Addition of homopolymers to the 3' ends of duplex DNA with terminal transferase. Methods Enzymol. 1979 68:41–50.

Nishihara, T., Mills, D. R., and Kramer, F. R. (1983) J. Biochem. 93:669–674. Localization of the Qβ Replicase Recognition Site in MDV-1 RNA.

Oi, V. T., Glazer, A. N. and Stryer, L. (1982) J. Cell. Biol. 93, 981–986.

Osterman, H. L and Coleman, J. E. (1981) Biochemistry 20, 4885–4892.

Pace, N. R., and Spiegelman, S. (1966) Science 153, 64–67. In vitro Synthesis of an Infectious Mutant RNA with a Normal RNA Replicase.

Palva, A. and Ranki, M. (1985) Clin. Lab. Med. 5, 475–490.

Pellegrino, M. G., Lewin, M., Meyer, III, W. A., Lanciotti, R. S., Bhaduri-Hauck, L., Volsky, D. J., Sakai, K., Folks, T. M., and Gillespie, D. (1987) A Sensitive Solution Hybridization Technique for Detecting RNA in Cells: Application to HIV in Blood Cells Biotechniques 5:452–459.

Poiesz, B. J., Ruscetti, F. W., Gazdar, A. F., Bun, P. A., Minna, J. D., and Gallo, R. C. (1980) Proc. Natl. Acad. Sci. USA 77, 7415–7419. Detection and Isolation of Type C Retrovirus Particles from Fresh and Cultured Lymphocytes of a patient with Cutaneous T-cell Lymphoma.

Popovic, M., Sarnagadharan, M. G., Read, E., and Gallo, R. C. (1984) Science 224, 497–500. Detection, Isolation, and Continous Production of Cytopathic Retroviruses (HTLV-III) from Patients with AIDS and pre-AIDS.

Priano, C., Kramer, F. R., and Mills, D. R. (1987) Cold Spring Harbor Symp. Quant. Biol. 52, 321–339. Evolution of the RNA Coliphages: The Role of Secondary Structures during RNA Replication.

Priano, C., Mills, D. R., and Kramer, F. R. (1989) Nucleic Acids Res., in preparation. Sequence, Structure, and Evolution of a 77-Nucleotide Template for Qβ Replicase.

Ranki, M. Palva, A., Virtanen, M., Laaksonen, M., and Soderlund, H. (1983) Gene 21, 77–85. Sandwich Hybridization as a Convenient Method for Detection of Nucleic Acids in Crude Samples.

Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, Jr., S. R., Pearson, M. L., Sautenberger, J. A., Papas, T. Sa. Ghrayeb, J., Chang, N. T., Gallo, R. C., and Wong-Staal, F. (1985) Nature 313, 277–284. complete Nucleotide Sequence of the AIDS Virus, HTLV-III.

Saiki, R. K., Scharf, S., Faloona, F., Mullis, K. B., Horn, G. T., Erlich, H. A., and Arnheim, N. (1985) Science 230, 1350–1354. Enzymatic Amplification of β-Globin Genomic Sequences and Restriction Site Analysis for Diagnosis of Sickle Cell Anemia.

Saiki, R. K., Gelfand, D. H., Stoffel, S., Scharf, S. J., Higuchi, R., Horn, G. T., Mullis, K. B., and Erlich, H. A. (1988) Science 239, 487–491. Primer-directed Enzymatic Amplification of DNA with a Thermostable DNA Polymerase.

Sammons, D. W., Adams, L. D. and Nishizawa, E. E. (1981) Electrophoresis 2, 135–141.

Sanger, F., Nicklen, S., and Coulson, A. K. (1977) Proc. Natl. Acad. Sci, USA 74, 5463–5467. DNA Sequencing with Chain-terminating Inhibitors.

Schaffner, W., Ruegg, K. J., and Weissmann, C. (1977) J. Mol. Biol. 117, 877–907. Nanovariant RNAs: Nucleotide Sequence and Interaction with Bacteriophage Qβ Replicase.

Seiki, M., Hattori, S., Hirayaman, Y., and Yoshida, M. (1983) Proc. Natl. Acad. Sci. USA 80, 3618–3622. Human Adult T-cell Leukemia Virus: Complete Nucleotide Sequence of the Provirus Genome Integrated in Leukemia Cell DNA.

Sharop, P. A., Sugden, B. and Sambrook, J. (1973) Biochemistry 12, 3055–3063.

Shimotohno, K., Takahashi, Y., Shimizu, N., Gojobori, T., Golde, D. W., Chen, I. S. Y., Miwa, M., and Sugimura, T. (1985) Proc. Natl. Acad. Sci. USA 82, 3101–3105. Complete Nucleotide Sequence of an Infectious Clone of Human T-cell Leukemia virus Type II: An Open Reading Frame for the Protease Gene.

Shore, D., Langowski, J., and Baldwin, R. L. (1981) Proc. Natl. Acad. Sci. USA 78, 4833–4837. DNA Flexibility Studied by Covalent Closure of Short Fragments into Circles.

Spiegelman, S., Haruna, I., Holland, I. B., Beardreau, G., and Mills, D. R. (1965) Proc. Natl. Acad. Sci. USA 54, 919–927. The Synthesis of a Self-propogating and Infectious Nucleic Acid with a Purified Enzyme.

Spiegelman, S., Pace, N. R., Mills, D. R., Levisohn, R. Eikhom, T. S., Taylor, M. M., Peterson, R. L., and bishop, D. H. L. (1968) Cold Spring Harbor Symp. Quant. Biol. 33, 101–124. The Mechanism of RNA Replication.

Syvanen, A.-C., Laaksonen, M., and Soderlund, H. (1986) Nucleic Acids Res. 14, 5037–5048. Fast Quantification of Nucleic Acid Hybrids by Affinity-based Hybrid Collection.

Thompson, J., and Gillespie, D. (1987) Anal. Biochem. 163, 281–291. Molecular Hybridization with RNA Probes in Concentrated Solutions of Guanidine Thiocyanate.

Tullis, R. H. and Rubin, H. (1980) Anal. Biochem. 107, 260–264.

Uhlenbeck, O. C. (1987) Nature 328, 596–600. A Small Catalytic Oligoribonucleotide.

Ulanovsky, L., Bodner, M., Trifonov, E. N., and Choder, M. (1986) Proc. Natl. Acad. Sci. USA 83, 862–866. Curved DNA: Design, Synthesis, and Circularization.

Urdea, M. S., Running, J. A. Horn, T., Clyne, J., Ku, L. and Warner, B. D. (1987) Gene 61, 253–264.

Wallace, R. B., Johnson, M. J., Suggs, S. V., Miyashi, K., Bhatt, R., and Itakura, K. (1981) Gene 16, 21026. A Set of Oligodeoxyribonucleotide Primers for DNA Sequencing in the Plasmid Vector pBR322.

Weissmann, C., Feix, G., and Slor, H. (1968) Cold Spring Harbor Symp. Quant. Bio. 33, 83–100. In vitro Synthesis of Phage RNA: The Nature of the Intermediates.

Zolg, J. W., Andrade, L. E. and Scott, E. D. (1987) Mol. Biochem. Parasitol. 22, 145–151.

Zuker, M., and Stiegler, P. (1981) Nucleic Acids Res. 9, 133–148. Optimal Computer folding of Large RNA Sequences using Thermodynamics and Auxiliary Information.

What is claimed is:

1. A method for determining the presence or concentration of an oligo- or polynucleotide of interest in a sample, comprising the steps of:
   (a) incubating the sample with replicatable and hybridizable recombinant single-stranded RNA probe molecules comprising:
      (1) a recognition sequence for the binding of an RNA-directed RNA polymerase;
      (2) a sequence required for the initiation of product strand synthesis by a polymerase; and
      (3) a heterologous RNA sequence (i) inserted in an externally located hairpin loop and (ii) complementary to the oligo- or polynucleotide of interest;
   under suitable conditions and for a sufficient period of time to permit complementary nucleotide sequences to hybridize, so as to thereby form a specific complex between a replicatable and hybridizable single-stranded RNA probe molecule and each oligo- or polynucleotide of interest in the sample;
   (b) removing unhybridized recombinant-RNA probe molecules from the reaction mixture;
   (c) incubating the reaction mixture with an RNA-directed RNA polymerase capable of synthesizing complementary copies of the recombinant-RNA probe molecules that are hybridized to the oligo- or polynucleotide of interest under conditions such that the complementary copies so synthesized are separated from the recombinant RNA probe molecules, and serve as templates for synthesis of identical copies of the recombinant-RNA probe molecules;
   (d) repeating step (c) at least once; and
   (e) detecting complementary and identical copies of the recombinant-RNA probe molecules so synthesized in step (c), thereby determining the presence or concentration of the oligo- or polynucleotide of interest.

2. A method of claim 1, wherein the oligo- or polynucleotide in the sample is bound to a solid support.

3. A method of claim 2, wherein the solid support is a nitrocellulose or nylon membrane.

4. A method of claim 1, wherein in step (a) the oligo- or polynucleotide of interest and the recombinant-RNA probe molecule are in solution.

5. A method of claim 4, wherein in step (b) the hybridized recombinant-RNA probe molecules are separated from the unhybridized probe molecules through the capture of the oligo- or polynucleotide onto a solid support.

6. A method of claim 5 wherein the hybridized recombinant-RNA probe molecules are separated from the unhybridized probe molecules by:
   (a) capturing the oligo- or polynucleotide of interest onto a solid support comprising paramagnetic particles linked to oligo(dT) groups which are bound to the 3' poly(dA) tails of capture probes, the capture probes also comprising a sequence complementary to a sequence of the oligo- or polynucleotide of interest located close to the sequence of the oligo- or polynucleotide of interest that is specifically complexed to the recombinant-RNA probe molecule by hybridizing the oligo- or polynucleotide of interest to the complementary sequence of the capture probes;

(b) placing the resulting reaction mixture in a magnetic field that draws the paramagnetic particles bound to the capture probe bound to the oligo- or polynucleotide of interest specifically complexed to the recombinant-RNA probe molecule to the walls of the container in which the reaction mixture is placed; and (c) withdrawing supernatant containing the unhybridized recombinant-RNA probe particles from the reaction mixture.

7. A method of claim 1 wherein detecting is carried out by the incorporation of radioactively labelled ribonucleoside 5'-triphosphate precursors into the recombinant-RNA products.

8. A method of claim 1 wherein detecting is carried out by the incorporation of chemically modified ribonucleoside 5'-triphosphate precursors into the recombinant-RNA products.

9. A method of claim 8, wherein the chemically modified ribonucleoside 5'-triphosphate precursors are biotinylated.

10. A method of claim 8, wherein the chemically modified ribonucleoside 5'-triphosphate precursors are fluorescent.

11. A method of claim 1, wherein detecting is carried out by the binding of RNA-specific chromogenic or fluorogenic dyes to the recombinant-RNA products.

12. A method of claim 1, wherein detecting is carried out by physical methods.

13. A method of claim 1, wherein in step (c) the RNA-directed RNA polymerase is Qβ replicase.

14. A method of claim 1 wherein the sample is a tissue specimen.

15. A method of claim 1 wherein the tissue specimen is a blood specimen.

16. A method of claim 1 wherein in step (a) the conditions for hybridization comprise exposing the sample to guanidine thiocyanate.

17. A method of claim 1, wherein the time of incubation in step (c) is sufficiently short so that the number of recombinant-RNA product strands does not exceed the number of polymerase molecules, with the result that the number of recombinant-RNA product molecules is proportional to the logarithm of the number of recombinant-RNA probe molecules originally hybridized.

18. A method of claim 17 wherein the concentration of the oligo- or polynucleotide of interest detected in step (d) is measured by determining the intensity of the chromogenic or fluorescent signal in a reaction mixture in logarithmic phase at multiple time-points as the reaction proceeds and determining the concentration of the labelled recombinant-RNA products thereby, preparing a standard curve relating the concentration of the oligo- or polynucleotide of interest to the length of time of the reaction using a standard equation, and using the standard curve to determine the concentration of the oligo- or polynucleotide of interest at a known time point in the reaction.

19. An automated method of claim 18.

20. A method of claim 1, wherein the time of incubation in step (c) is sufficiently long so that the number of recombinant-RNA product strands exceeds the number of polymerase molecules, with the result that the number of recombinant-RNA product molecules is linearly proportional to the number of recombinant-RNA probe molecules originally hybridized.

21. A method of claim 20 wherein the concentration of the oligo- or polynucleotide of interest detected in step (d) is determined by preparing standards containing a known amount of recombinant-RNA probe molecules and directly relating the amount of recombinant-RNA product strands present in the hybridization reaction at a given time in the linear phase of the hybridization reaction to the logarithm of the number of recombinant-RNA probe molecules originally hybridized by using the known standards.

22. A method for simultaneously determining the presence or concentration of several different oligo- or polynucleotides of interest in a sample, comprising the steps of:

(a) incubating the sample with a mixture of different types of replicatable and hybridizable recombinant single-stranded RNA probe molecules comprising:

(1) a recognition sequence for the binding of an RNA-directed RNA polymerase;

(2) a sequence required for the initiation of product strand synthesis by a polymerase; and (3) a heterologous RNA sequence (i) inserted in an externally located hairpin loop and (ii) complementary to one of the oligo- or polynucleotides of interest each type having a different inserted sequence, under suitable conditions and for a sufficient period of time to permit complementary nucleotide sequences to hybridize, so as to thereby form specific complexes between replicatable and hybridizable recombinant single-stranded RNA probe molecules from the mixture and the oligo- or polynucleotides of interest in the sample;

(b) removing unhybridized recombinant-RNA probe molecules from the reaction mixture;

(c) incubating the reaction mixture with an RNA-directed RNA polymerase capable of synthesizing complementary copies of the recombinant-RNA probe molecules that are hybridized to the oligo- or polynucleotides of interest under conditions such that the complementary copies so synthesized are separated from the recombinant-RNA probe molecules, and serve as templates for synthesis of identical copies of the recombinant-RNA probe molecules;

(d) repeating step (c) at least once;

(e) separating the mixture of the complementary and identical copies of the recombinant-RNA probe molecules so synthesized by hybridizing them to an ordered array of polynucleotides bound to a solid support, where each of the polynucleotides is complementary to one type of the complementary or identical copies of the recombinant-RNA probe molecules so synthesized; and (f) detecting the complementary or identical copies of the recombinant-RNA probe molecules separated in step (e), thereby determining the presence or concentration of each oligo- or polynucleotide of interest.

23. The method of claim 22 wherein the sample is a tissue specimen.

24. The method of claim 23 wherein the tissue specimen is a blood specimen.

25. A method of claim 23 wherein in step (a) the conditions for hybridization comprise exposing the sample to guanidine thiocyanate.

26. A method of claim 23 wherein the solid support is a membrane.

* * * * *